(12) United States Patent
Ishida et al.

(10) Patent No.: US 12,011,517 B2
(45) Date of Patent: *Jun. 18, 2024

(54) AIR FRESHENING PRODUCT

(71) Applicant: The Procter & Gamble Company, Cincinnati, OH (US)

(72) Inventors: Yoshiki Ishida, Singapore (BE); Gaurav Saini, Singapore (BE); Rahul Vyas, Singapore (BE); Garima Chauhan, Singapore (BE)

(73) Assignee: The Procter & Gamble Company, Cincinnati, OH (US)

( * ) Notice: Subject to any disclaimer, the term of this patent is extended or adjusted under 35 U.S.C. 154(b) by 803 days.

This patent is subject to a terminal disclaimer.

(21) Appl. No.: 17/064,647

(22) Filed: Oct. 7, 2020

(65) Prior Publication Data
US 2021/0106710 A1    Apr. 15, 2021

Related U.S. Application Data

(60) Provisional application No. 62/913,170, filed on Oct. 10, 2019.

(51) Int. Cl.
*A61L 9/013* (2006.01)
*A01N 35/02* (2006.01)
(Continued)

(52) U.S. Cl.
CPC .............. *A61L 9/013* (2013.01); *A01N 35/02* (2013.01); *A01N 65/22* (2013.01); *A61L 9/04* (2013.01);
(Continued)

(58) Field of Classification Search
CPC .................. A61N 35/02; A01N 35/02
See application file for complete search history.

(56) References Cited

U.S. PATENT DOCUMENTS

4,502,630 A * 3/1985 Haworth .................. A61L 9/12
239/34
5,795,566 A  8/1998 Joulain et al.
(Continued)

FOREIGN PATENT DOCUMENTS

EP  2008637 A1  12/2008
EP  3197426 A1  8/2017
(Continued)

OTHER PUBLICATIONS

PCT Search Report and Written Opinion for PCT/US2020/070623 dated Feb. 22, 2021.
(Continued)

*Primary Examiner* — Benjamin J Packard
(74) *Attorney, Agent, or Firm* — Carolyn S. Powell

(57) ABSTRACT

An antibacterial air freshening product for an interior environment. The product includes a container containing 1 ml to 50 ml of a freshening composition in fluid communication with a membrane. The composition is substantially free of a surfactant and has from 0.5% to 20% of a volatile aldehyde mixture, by weight of the composition. The volatile aldehyde mixture includes a C5 to C8 unbranched unsubstituted linear alkenal and a C9 to C14 unbranched unsubstituted linear alkenal. A weight ratio of the C5 to C8 unbranched unsubstituted linear alkenal to the C9 to C14 unbranched unsubstituted linear alkenal is from 3:1 to 1:3.

17 Claims, 11 Drawing Sheets

(51) Int. Cl.
   *A01N 65/22*   (2009.01)
   *A61L 9/04*    (2006.01)
   *A61L 9/12*    (2006.01)
   *B60H 3/00*    (2006.01)
   *B60H 3/06*    (2006.01)

(52) U.S. Cl.
   CPC .............. *A61L 9/12* (2013.01); *B60H 3/0014* (2013.01); *B60H 3/0608* (2013.01); *A61L 2209/131* (2013.01); *A61L 2209/135* (2013.01)

(56)           References Cited

U.S. PATENT DOCUMENTS 7,603,726 B2    10/2009   Sewalski et al.
   2017/0274110 A1  9/2017   Nwachukwu
   2019/0134245 A1  5/2019   Vyas

FOREIGN PATENT DOCUMENTS

| JP | 2002179509 A | 6/2002 |
| JP | 2017530122 A | 10/2017 |
| WO | 9014849 A1 | 12/1990 |
| WO | 2011084463 A1 | 7/2011 |
| WO | 2011149851 A1 | 12/2011 |
| WO | 2012054939 A2 | 4/2012 |
| WO | 2013176925 A1 | 11/2013 |
| WO | 2019089739 A1 | 5/2019 |

OTHER PUBLICATIONS

Boelens "Organoleptic properties of aliphatic aldehydes" Perfumer & Flavorist, vol. 12, No. 5, Jan. 1, 1987, pp. 31-43.

Giuseppe Bisignano et al. "In vitro antibacterial activity of some aliphatic aldehydes from *Olea europaea* L", FEMS Microbiology Letters, vol. 198, No. 1, Apr. 1, 20021, pp. 9-13.

* cited by examiner

AIR FRESHENING PRODUCT

FIELD OF THE INVENTION

The present invention relates generally to air freshening products and methods for preventing bacteria growth in an interior environment.

BACKGROUND OF THE INVENTION

It is known that fecal waste matter contains bacteria which generate malodor. Fecal waste matter may be found in spaces including but not limited to small spaces, small rooms, or pet carriers. Small rooms may include but are not limited to bathroom, toilet, locker rooms or the like. Small spaces may include but are not limited to storage spaces for garbage, toilet bowls, closets, furniture for storage of shoes, sneakers or the like, cat litter, pet litter boxes, pet cages, pet bedding, gym lockers, or the like. Pet carriers are small portable boxes, crates, or cages used to transport small animals such as cats, lap dogs, hamsters, guinea pigs or the like, from one location to another.

For example, malodor in toilets typically originate from the use of the toilet bowl as it is used to contain fecal waste matter dispelled by humans. The fecal waste matter contains bacteria which is the primary malodor source (source that actually produce malodor) in the toilet. When the toilet bowl is flushed, the bacteria molecules tend to become quickly distributed above and about the interior area of the toilet and settle on surfaces in the toilet including but not limited to permeable materials such as terry towel, vinyl floor mats, wallpaper or the like. Such surfaces containing the bacteria molecules become secondary malodor sources.

Fragrance dispensing in the immediate area of the toilet using conventional air fresheners described hereinbefore have been fairly effective in masking the malodors arising from the primary malodor source. Further, toilet bowl cleaning dispensers have been developed to clean and freshen the toilet bowl after use. One type of dispenser for spraying an inner surface of a toilet bowl with a cleaning and/or deodorizing chemical is described in U.S. Pat. No. 7,603,726B2 (Assignee: S.C. Johnson & Son, Inc). However, U.S. Pat. No. 7,603,726B2 describe that the dispenser works by introducing active substances into toilet water to create an environment within the toilet bowl for cleaning and do not necessarily help to prevent bacteria growth on secondary malodor sources not within the toilet bowl. An antimicrobial composition including at least one aliphatic aldehyde component and allyl isothiocyanate for reducing the bacterial activity of an environment is described in International Patent Publication No. WO 2011/149851A1 (Assignee: Takasago International Corporation).

Further, there is also a continuing need to provide users a "well balanced" scent experience that generally include high, middle, and base scent "notes.".

Accordingly, there is a need to provide an air freshening product that help to prevent bacteria growth (thereby mitigating against bacterial malodor) while also providing a well-balanced perfume experience that users expect to enjoy in their air freshening products.

SUMMARY OF THE INVENTION

The present invention relates to an antibacterial air freshening product for an interior environment, wherein the interior environment is a finite volume of space in a non-vehicle environment, the product comprising:

a container containing 1 ml to 50 ml of a freshening composition in fluid communication with a delivery member configured to contain a liquid phase of the composition and allow the liquid phase of the composition to evaporate therefrom:
wherein the composition is substantially free of a surfactant and comprises: from 0.5% to 20% of a volatile aldehyde mixture, by weight of the composition;
wherein the volatile aldehyde mixture consists of:
(i) a C5 to C8 unbranched unsubstituted linear alkenal; and
(ii) a C9 to C14 unbranched unsubstituted linear alkenal, wherein a weight ratio of the C5 to C8 unbranched unsubstituted linear alkenal to the C9 to C14 unbranched unsubstituted linear alkenal is from 3:1 to 1:3.

DETAILED DESCRIPTION OF THE INVENTION

Figure 1:
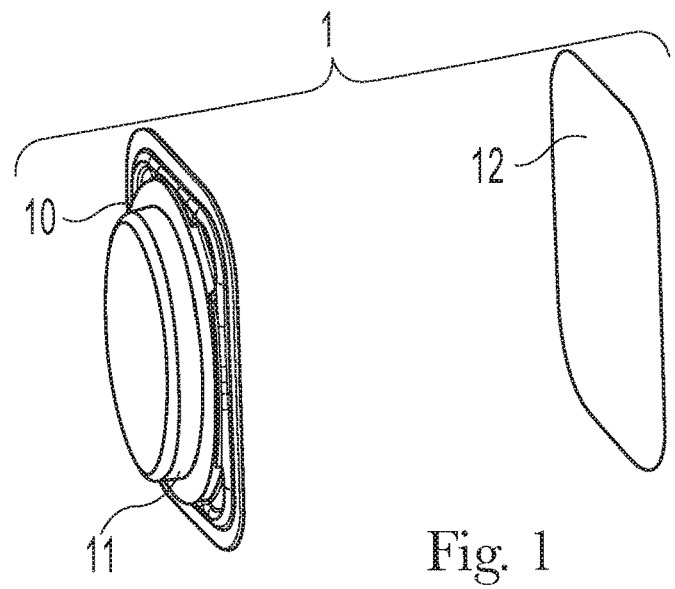
FIG. 1 is a perspective view of components of a device for an air freshening composition for an antibacterial air freshening product according to the present invention.

The present invention relates to air freshening products with improved antibacterial properties for preventing bacterial growth on surfaces comprising a permeable material in an interior environment in a continuous manner. Specifically, an antibacterial air freshening product (hereinafter "product") comprises a reservoir for containing a liquid phase or a solid phase of a freshening composition (hereinafter "composition") having a volatile aldehyde mixture for bacteria growth prevention on a surface comprising a permeable material. The volatile aldehyde mixture comprises C5 to C8 unbranched unsubstituted linear alkenal and C9 to C14 unbranched unsubstituted linear alkenal which can evaporate in passive air flow conditions continuously can deposit on surfaces having a permeable material which have bacteria/bacterium deposited thereon and the deposited volatile aldehyde mixture prevents bacteria growth on the permeable material.

A technical effect of the volatile aldehyde mixture of C5 to C8 unbranched unsubstituted linear alkenal and C9 to C14 unbranched unsubstituted linear alkenal is the mixture can measurably prevent bacteria growth on the permeable material (e.g. by in vitro microbiology testing by simulating the environment of an interior space in an interior environment demonstrated in results as described hereinafter under Examples) thereby reducing bacterial malodor rather than merely covering up or masking the bacterial malodor. In the short term, a bacteria growth prevention effect of the composition can reduce the level of malodors in the air that are currently being sensed by, for example, a human. In the longer term, the invention can prevent bacteria growth on surfaces comprising permeable materials in the interior environment.

It has also been surprisingly found that formulating C5 to C8 unbranched unsubstituted linear alkenal and C9 to C14 unbranched unsubstituted linear alkenal in a weight ratio of 3:1 to 1:3 in a composition according to the present invention enables release of the above volatile aldehydes from the product in a tandem manner thereby enabling deposition of C5 to C8 unbranched unsubstituted linear alkenal and C9 to C14 unbranched unsubstituted linear alkenal on surfaces comprising a permeable material having bacteria deposited thereon to prevent growth of bacteria on the permeable material thereby reducing bacterial malodor in the interior environment.

Specifically, having two different types of alkenals instead of one single alkenal increases longevity of a bacteria growth prevention benefit because the C5 to C8 unbranched unsubstituted linear alkenal and the C9 to C14 unbranched unsubstituted linear alkenal have different vaporization rates and can act in tandem to enhance an overall bacterial growth prevention efficacy in a sequential manner. Exemplary alkenals are listed in the following description and are named according to the method of naming organic chemical compounds as recommended by the International Union of Pure and Applied Chemistry (IUPAC).

In the following description, the product described is a consumer product, such as a toilet deodorizer, for evaporating a freshening composition in an interior occupancy space of a bathroom containing a toilet to deliver a variety of benefits such as bacteria growth prevention, freshening, malodor removal or scenting of air in the bathroom. However, it is contemplated that the product may be configured for use in a variety of applications to deliver a freshening composition to provide the benefits in interior environments such as rooms in household and commercial establishments or furniture for storage of household items, and the air freshening product may include but is not limited to consumer products, such as, for example air freshening products, air fresheners or the like.

The product may also comprise a delivery member configured to contain a liquid phase of the composition and allow the liquid phase of the composition to evaporate therefrom. The delivery member may include a wick, a membrane, gel, porous or semi-porous substrate including a felt pad. An exemplary delivery member may be a membrane which is a semi-permeable material which allows some components of matter to pass through but stops other components. Of the components that pass through, the membrane moderates the permeation of components i.e. some components permeate faster than other components. Such components may include molecules, ions or particles.

For the purposes of illustrating the present invention in detail, the invention is described below as a non-energized antibacterial air freshening product having a membrane in fluid communication with the composition. However, it will be appreciated that the composition may be delivered from the product to the space through a wick. Further, the product of the present invention can be energized or non-energized. Prior to describing the present invention in detail, the following terms are defined for clarity. Terms not defined should be given their ordinary meaning as understood by a skilled person in the relevant art.

"Horizontal orientation" as used herein, refers to a position of an antibacterial air freshening product according to the present invention wherein the membrane is facing the environment in an upward or downward position.

"Interior environment" refers to a finite volume of space in a non-vehicle environment. The interior environment may be a room in a residential or commercial environment such as for example a sanitary facility. The sanitary facility may include a bathroom, a toilet, a bathroom containing a toilet, a locker room. The interior environment may also be an enclosed space such as for example, furniture for storage of personal items including but not limited to shoe cabinets, wardrobes, gym lockers, as well as pet litter boxes, cat litter, pet cages, pet carriers. Pet carriers are small portable boxes, crates, or cages used to transport small animals such as cats, lap dogs, hamsters, guinea pigs or the like, from one location to another.

"Membrane" as used herein, refers to a semi-permeable material which allows some components of matter to pass through but stops other components. Of the components that pass through, the membrane moderates the permeation of components i.e. some components permeate faster than other components. Such components may include molecules, ions or particles.

"Microporous membrane" as used herein, refers to a material having a network of pores.

"Natural convection" as used herein, refers to a type of flow, of motion of a liquid such as water or a gas such as air, in which the fluid motion is not generated by any external source (like a pump, fan, suction device, etc.) but by some parts of the fluid being heavier than other parts.

"Non-energized" means that the product is passive and does not require to be powered by a source of external energy. In particular, the product does not need to be powered by a source of heat, gas or electrical current. The product may also be configured as an energized device. An exemplary energized device may be an electrical device. The energized device may be an electrical car outlet or battery-operated air freshener having a wick and/or a membrane as described in the following description to transport a freshening composition and/or evaporate a freshening composition therefrom; or other heating devices (e.g. devices powered by chemical reactions such as catalyst fuel systems; solar powered devices, etc.).

"Permeable material" as used herein, refers to any material that allows liquids or gases to pass through, and includes, but is not limited to, drywall, wall paper, wood, vinyl, plastic, plaster, wallboard, fabrics, upholstery, paper, wovens, natural polymers, synthetic polymers and inorganic materials and mixtures thereof. The permeable material may also include residue formed on any inanimate surface, and includes but is not limited to dust particles or grease on the inanimate surface.

As used herein, the term "inanimate surface" refers to surfaces including but not limited to fabrics, carpets, household surfaces such as floors, walls, carpet padding, towels and the like.

"Vertical orientation" as used herein, refers to a position of an antibacterial air freshening product according to the present invention wherein the membrane is facing the environment in a forward facing position or in a rear facing position.

"Freshening composition" as used herein, refers to a material that is vaporizable at room temperature and atmospheric pressure without the need of an additional energy source. The composition may be configured for various uses, including but not limited to, air freshening, deodorization, odor elimination, malodor counteraction, pest control, insect control, insect repelling, medicines/medicaments, disinfectants, sanitization, mood enhancement, aromatherapy aid, scented compositions, non-scented compositions, or any other use which requires a freshening composition that acts to condition, modify, or otherwise change the atmosphere or the environment. Further, it is not necessary for all of the component materials of the composition to be volatile. Any suitable composition in any amount or form, including a liquid, solid, gel or emulsion, may be used. Materials suitable for use herein may include non-volatile compounds, such as carrier materials (e.g., water, solvents, etc.). It should also be understood that when the composition is described herein as being "delivered", "emitted", or "released", this refers to the volatization of the volatile component thereof, and does not require that the non-volatile components thereof be emitted.

Figure 2:
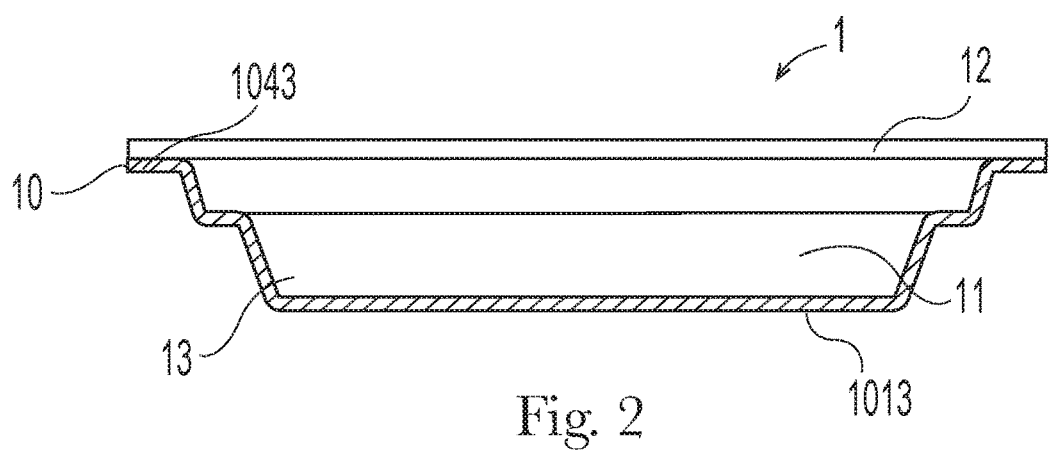
FIG. 2 is a side section view of an antibacterial air freshening product according to the present invention in a horizontal orientation when the product is placed on a support.

FIG. 1 is a perspective view of components of a device 2 for containing a freshening composition 13 (hereinafter "composition") which upon assembly and filling with the composition 13, defines an antibacterial air freshening product 1 (an exemplary example is shown in FIG. 2) according to the present invention. Referring to FIGS. 1 and 2, the device 2 comprises a container 10 containing a reservoir 11 for containing the freshening composition 13. The container 10 may be made of a substantially vapor impermeable material designed to resist diffusion of a vapor phase of the composition 13. For example, the container 10 may be made of metal, glass, ceramic, porcelain, tile and plastic including but not limited to thermoplastics and other known materials suitable for thermoforming, injection molding and blow molding. A delivery member 12, such as for example, a membrane 12 may be disposed within the container 10 and arranged to be in fluid communication with the composition 13.

FIG. 2 is a side section view of the antibacterial air freshening product 1 (hereinafter "product") in a horizontal orientation when the product 1 is placed on a support. The product 1 can be constructed as a disposable, single-use item or one that it is replenished with a composition 13.

The product 1 may further include a vapor impermeable substrate 14 adjacent to the membrane 12 wherein the vapor impermeable substrate 14 is configured to prevent release of the composition 13 before use. The product 1 may be configured for use in any desired orientation, including but not limited to a vertical orientation such as shown in FIG. 3.

Figure 3:
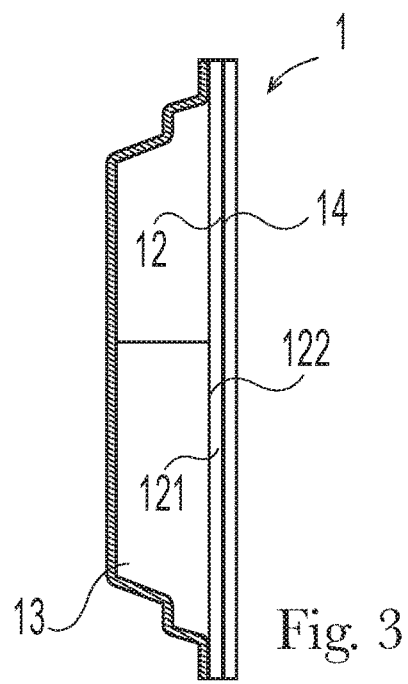
FIG. 3 is a side section view of the product as shown in FIG. 1 in a vertical orientation when the product is placed on a support.

FIG. 3 shows a side schematic view of the product 1 of FIG. 2 wherein the product 1 is substantially the same as the product 1 of FIG. 2 except that when the product 1 is in use, the membrane 13 comprises a membrane first surface 121 disposed in fluid communication with the composition 13 and a membrane second surface 122 facing the environment and away from the composition 13 when a vapor impermeable substrate 14 is removed when the user needs to activate the product 1.

Figure 7:
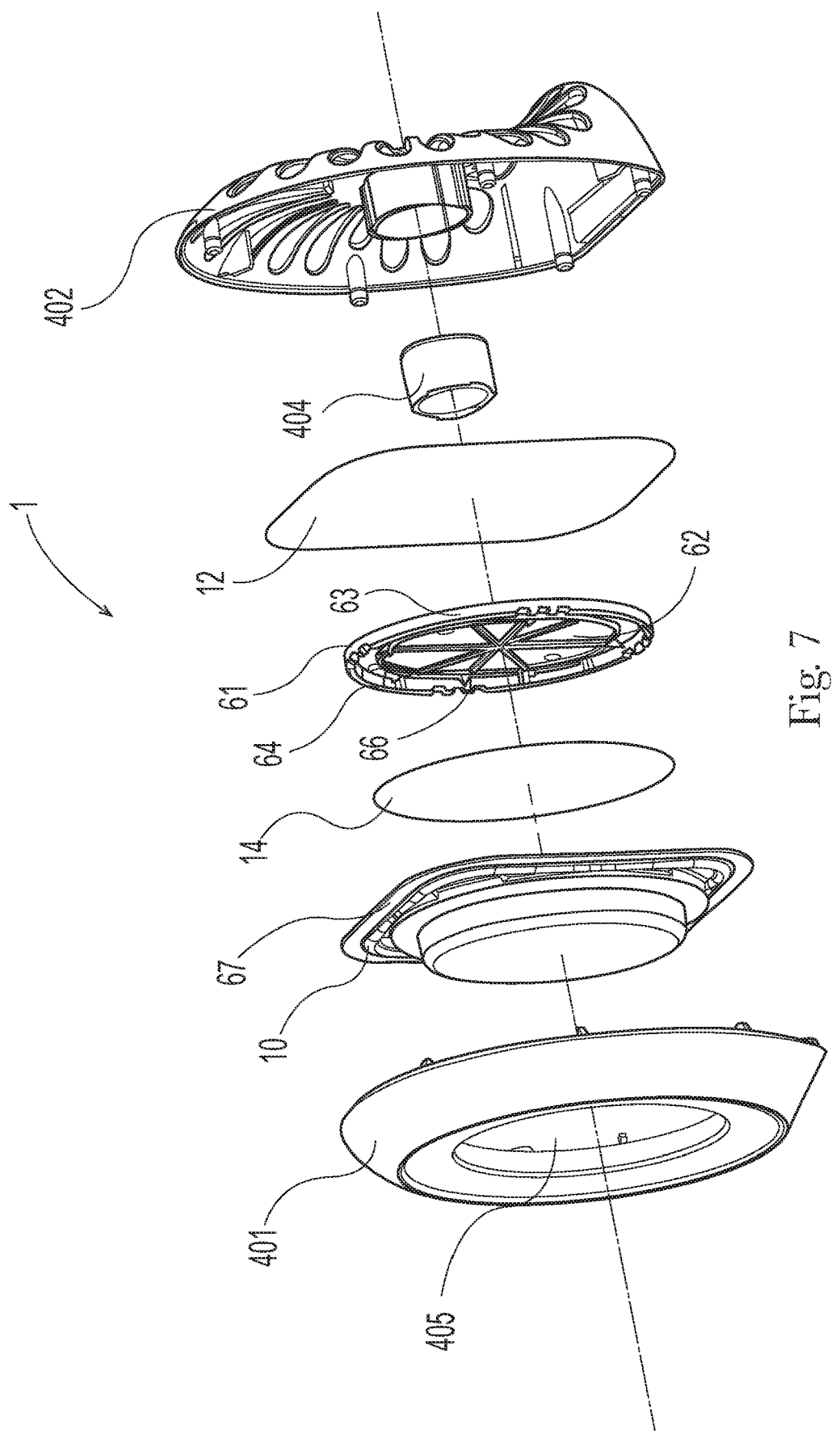
FIG. 7 is a perspective view of components of the product of FIG. 5.
Figure 8:
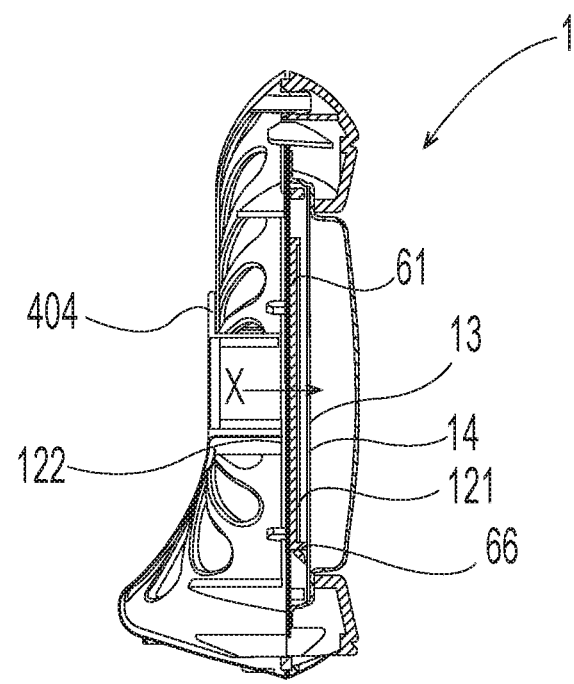
FIG. 8 is a side section view of the product of FIG. 5.

Referring to FIG. 3, a vapor impermeable substrate 14 may be releasably attached to a periphery of the membrane 12 to form a removeable cover for the product 1. The vapor impermeable substrate 14 may be rupturable to allow the composition 13 to pass through when ruptured. For example, as shown in FIGS. 7 and 8, the vapor impermeable substrate 14 may be a rupturable substrate 14 disposed adjacent to the membrane 12 and attached to an inner periphery of the container 10 to form a sealed reservoir adjacent the membrane 12.

The composition 13 comprises at least 0.25% of a C5 to C8 unbranched unsubstituted linear alkenal and at least 0.25% of a C9 to C14 unbranched unsubstituted linear alkenal, by weight of the composition 13. Providing a composition having a mixture of alkenals in the above ranges in a method according to present invention and an effective prevention of bacteria growth on surfaces is demonstrated in the Examples. Specifically, data in Example I shows that an Inventive Composition 1 having a C6 alkenal ((E)-2-Hexen-1-al) in an amount of 0.25% by weight of the composition and a C10 alkenal (4-Decen-1-al) in an amount of 0.25% by weight of the composition provides an antibacterial activity value of 1.98.

An exemplary C9-C14 unbranched unsubstituted linear alkenal may have a trans configuration, preferably a (E)-2 C9-C14 unbranched unsubstituted linear alkenal. An exemplary C5-C8 unbranched unsubstituted linear alkenal may have a trans configuration, preferably a (E)-2 C5-C8 unbranched unsubstituted linear alkenal. Without wishing to be bound by theory, an antimicrobial effectiveness of the above exemplary volatile aldehydes may be influenced by its chain length. Long chain aldehydes have broad antimicrobial spectrum. Between cis and trans configuration-cis configuration has side chains that create bends and shorten the length of carbon tail hence a trans configuration are more effective against bacteria and thereby providing improved antibacterial efficacy and improved bacteria growth prevention.

The C9-C14 unbranched unsubstituted linear alkenal may comprise a single double bond, preferably wherein the single double bond is in the C3, C4, or C5 position, more preferably the C3 or C4 position, yet more preferably the C4 position. The C5-C8 unbranched unsubstituted linear alkenal comprises a single double bond, preferably wherein the single double bond is in the C2, C3, or C4 position, more preferably the C2 or C3 position, yet more preferably the C2 position.

The C9-C14 unbranched unsubstituted linear alkenal comprise from 0.2%-10%, preferably from 0.2%-8%, yet more preferably from 0.2%-5%, by weight of the composition. The C5-C8 unbranched unsubstituted linear alkenal comprise 0.2%-10%, preferably from 0.2%-8%, yet more preferably from 0.2%-5%, by weight of the composition. Still further, the composition 13 may comprise a mixture of a C5 to C8 unbranched unsubstituted linear alkenal and a C9 to C14 unbranched unsubstituted linear alkenal, wherein the mixture is in an amount of 1.5% by weight of the composition.

The C9-C14 unbranched unsubstituted linear alkenal is C9-C12, preferably C9-C11, more preferably C10 unbranched unsubstituted linear alkenal. The C5-C8 unbranched unsubstituted linear alkenal is C5-C7, preferably C6 unbranched unsubstituted linear alkenal. Exemplary C5 to C8 Sunbranched unsubstituted linear alkenals which may be used include, but are not limited to, alkenals as shown in Table 1 below. Exemplary C9 to C14 unbranched unsubstituted linear alkenals which may be used include, but are not limited to, alkenals as shown in Table 2 below.

TABLE 1

| C5 to C8 unbranched unsubstituted linear alkenals | |
|---|---|
| CAS | IUPAC Name |
| 764-39-6 | 2-Penten-1-al |
| 5604-55-7 | 3-Penten-1-al |
| 2100-17-6 | 4-Penten-1-al |
| 6728-26-3 | (E)-2-Hexen-1-al |
| 16635-54-4 | (Z)-2-Hexen-1-al |
| 69112-21-6 | 3-Hexen-1-al |
| 25166-87-4 | 4-Hexen-1-al |
| 18829-55-5 | 2-Hepten-1-al |
| 89896-73-1 | 3-Hepten-1-al |
| 929-22-6 | 4-Hepten-1-al |
| 2363-89-5 | 2-Octen-1-al |
| 76595-71-6 | 3-Octen-1-al |
| 78693-35-3 | 4-Octen-1-al |

TABLE 2

| C9 to C14 unbranched unsubstituted linear alkenals | |
|---|---|
| CAS | IUPAC Name |
| 18829-56-6 | 2-Nonen-1-al |
| 31823-43-5 | 3-Nonen-1-al |
| 2277-16-9 | 5-Nonen-1-al |
| 3913-81-3 | 2-Decen-1-al |
| 65405-70-1 | 4-Decen-1-al |
| 60671-72-9 | 5-Decen-1-al |
| 2463-77-6 | 2-Undecen-1-al |
| 68820-32-6 | 4-Undecen-1-al |
| 4826-62-4 | 2-Dodecen-1-al |
| 68141-15-1 | 3-Dodecen-1-al |
| 21944-98-9 | 4-Dodecen-1-al |
| 68820-33-7 | 5-Dodecen-1-al |
| 7774-82-5 | 2-Tridencen-1-al |
| 98474-68-1 | 4-Tridecen-1-al |
| 64461-99-00 | 2-Tetradecen-1-al |

Table 3 shows a volatile aldehyde mixture of C5-C8 and C9 to C14 unbranched unsubstituted linear alkenals suitable for use in the composition of the present invention.

TABLE 3

| Exemplary Volatile Aldehyde Mixture | | | |
|---|---|---|---|
| CAS No. | IUPAC Name | Weight % by weight of the Composition | Average Vapor Pressure (Torr) at 25 degrees Celsius |
| 6728-26-3 | (E)-2-Hexen-1-al | 0.25% to 10% | 10.7 |
| 3913-81-3 | (E)-2-Decen-1-al | 0.25% to 10% | 0.0674 |

The C5-C8 and C9 to C14 unbranched unsubstituted linear alkenals according to the present invention may be selected for example from natural, essential oils or synthetic perfumes, and blends thereof. For example, the C5-C8 and C9 to C14 unbranched unsubstituted linear alkenals may be in a trans configuration and may be selected from compounds occurring naturally in the fruit and leaves of the olive (*Olea europea* L.). 2-decen-1-al is obtained from the group selected from: olive leaf essential oil, coriander leaf essential oil and blends thereof. (E)-2-hexen-1-al and/or (E)-2-decen-1-al may be obtained from the group selected from: olive leaf essential oil, coriander leaf essential oil and blends thereof.

The composition may, optionally, include odor masking agents, odor blocking agents, and/or diluents. "Odor blocking" refers to the ability of a compound to dull the human sense of smell. "Odor-masking" refers to the ability of a compound to mask or hide a malodorous compound. Odor-masking may include a compound with a non-offensive or pleasant smell that is dosed such it limits the ability to sense a malodorous compound. Odor-masking may involve the selection of compounds which coordinate with an anticipated malodor to change the perception of the overall scent provided by the combination of odorous compounds. Exemplary diluents include dipropylene glycol methyl ether, and 3-methoxy-3-methyl-1-butanol, and mixtures thereof. The composition may also, optionally, include perfume raw materials that solely provide a hedonic benefit (i.e. perfume raw materials which do not prevent bacteria growth yet provide a pleasant fragrance). The composition 13 may be comprised in a product 1 as shown in the figures according to the present invention. For the purposes of illustrating the present invention in detail, the invention is described below in connection with a toilet environment. However, it will be appreciated that the invention may be implemented in any interior environment comprising a surface having a permeable material with a bacterium deposited thereon.

To explain the way the product 1 works to provide bacteria growth prevention on a surface comprising a permeable material in an interior environment, it is helpful to understand how the product 1 is activated and how a vapor release rate of the composition 13 is generated. A method of preventing bacteria growth in an interior environment according to the present invention is described with reference to FIGS. 4A and 4B. The method includes providing an antibacterial air freshening product 1 in an interior environment 100 including a surface 101 comprising a permeable material 102 having a bacterium (not shown) disposed thereon. The interior environment 100 is under natural convection conditions.

Figure 4A:
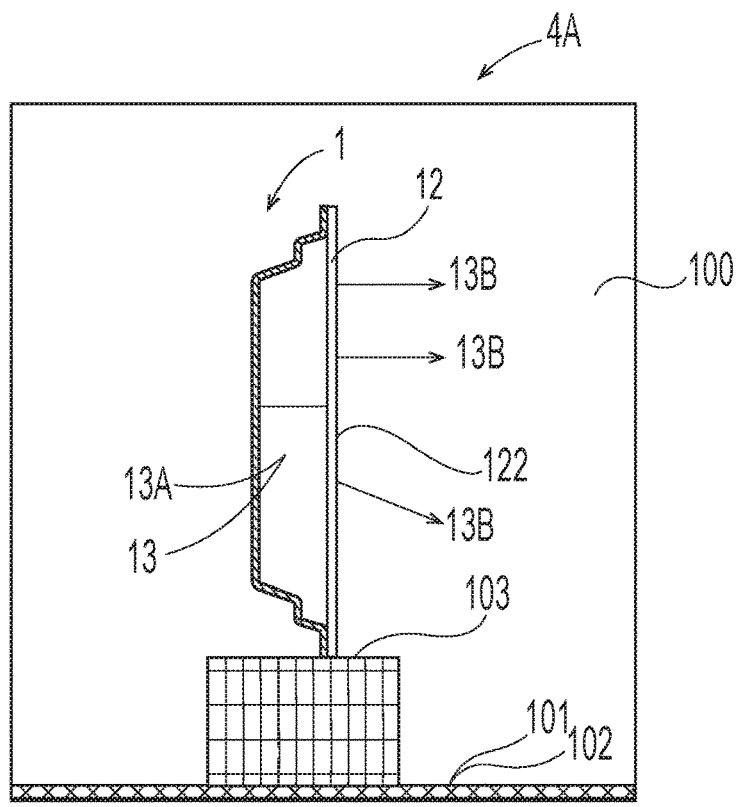
FIGS. 4A and 4B are schematic drawings which show the movement of a vapor phase of a freshening composition across the membrane in the product shown in FIG. 1 in an interior environment under natural convection conditions.
Figure 4B:
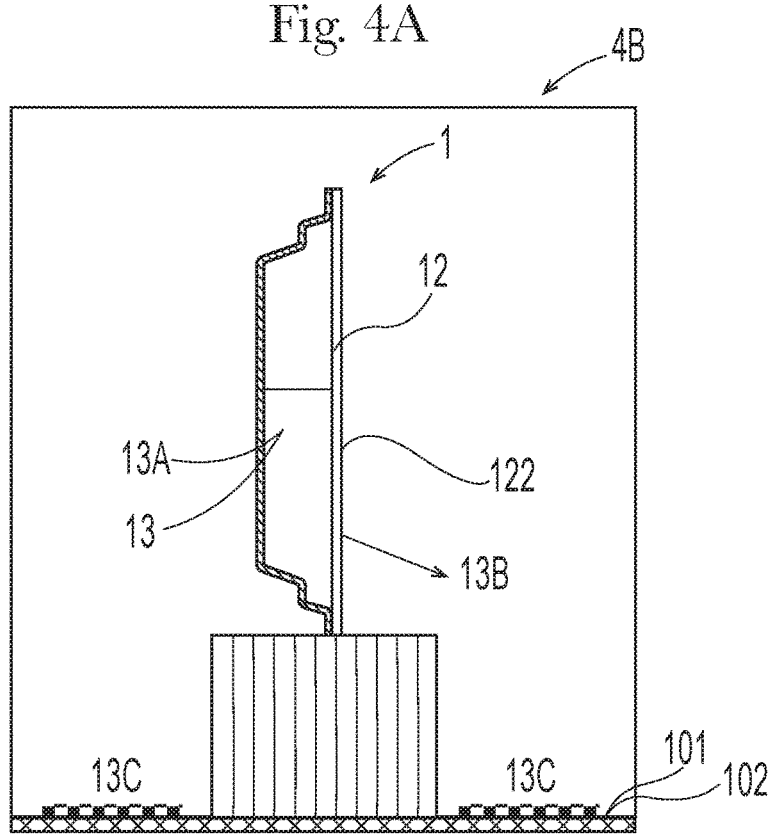

In FIGS. 4A and 4B, the product 1 is in a substantially vertical position when placed on a support 103 in the interior environment 100. The container 10 is partially filled with the composition 13. FIG. 4A illustrates a first step 4A of the method in which at least a portion of the membrane 12 is wetted such that a liquid phase 13A of the composition 13A and/or a vapor 13B of the composition 13 passes through the membrane 12 into the interior environment 100. FIG. 4B illustrates a second step 4B of the method in which molecules of the vapor 13B is deposited on the permeable material 102 having a bacterium disposed thereon.

Referring to FIG. 4A, a liquid phase 13A of the composition 13 passes through the membrane 12 from the membrane first surface 121 until a sufficiently high level of molecules is absorbed until a sufficiently high level of molecules is absorbed within the membrane 12. The liquid phase 13A of the composition 13 may wet the membrane 12 by means of capillary flow of the composition 13 into pores of the membrane 12. Once the membrane 12 is wetted, the liquid phase 13A of the composition 13 is disposed near or at the membrane second surface 122 such that the molecules near the membrane second surface 122 have enough kinetic energy to evaporate from the membrane second surface 122 under natural convection conditions and turn into a vapor phase of the composition ("vaporization") and form a vapor 13B that passes into the interior environment 100 as shown in FIGS. 4A and 4B.

FIG. 4B illustrates a second step 4B of the method in which the vapor 13B is formed in the interior environment 100 and molecules of the vapor 13B is deposited on a surface 101 comprising a permeable material 102 disposed within the interior environment 100. The permeable material 102 having a bacterium disposed thereon. Specifically, the vapor 13B is formed in the interior environment 100 for an effective amount of time sufficient to enable the concentration level of molecules in the vapor 13B to increase to a level such that the vapor molecules 13C are deposited on the permeable material 102 as shown in FIG. 4B. The deposited amount of vapor molecules 13C contains an effective amount of the C5 to C8 and C9 to C14 unsubstituted and unbranched linear alkenals for preventing growth of a bacterium disposed on the permeable material 102 on the surface 101. Thus, the present invention achieves a reduced bacteria activity level of each of the different bacterium on different treated permeable materials as described in FIGS. 10 to 15 corresponding to the respective Tables in Examples I to VI. The bacterium may be selected from the group consisting of: *S aureus, K pneumoniae, P mirabilis, E coli, Enterococcus hirae*. As shown in the Examples, the composition may comprise an antibacterial activity value of at least 1, preferably at least 2, more preferably at least 3 at the end of a time period of 1 to 24 hours, preferably at the end of a time period of 18 to 24 hours, more preferably at the end of a time period of 18 hours. The interior environment may be selected from the group consisting of: bathroom, toilet, locker room, furniture for storage of household items, pet litter boxes, cat litter, pet cages, pet carriers, preferably the interior environment is the bathroom or the toilet.

The interior environment may comprise a surface having a permeable material selected from the group consisting of: fabrics, drywall, wovens, paper, natural polymers, synthetic polymers and inorganic materials and mixtures thereof, preferably the permeable material is selected from the group consisting of: terry towel, cotton, vinyl and combinations thereof.

The above described method of the present invention can be used to deliver an antibacterial air freshening composition for bacteria growth prevention in a substantially continuous way under natural convection conditions.

Figure 5:
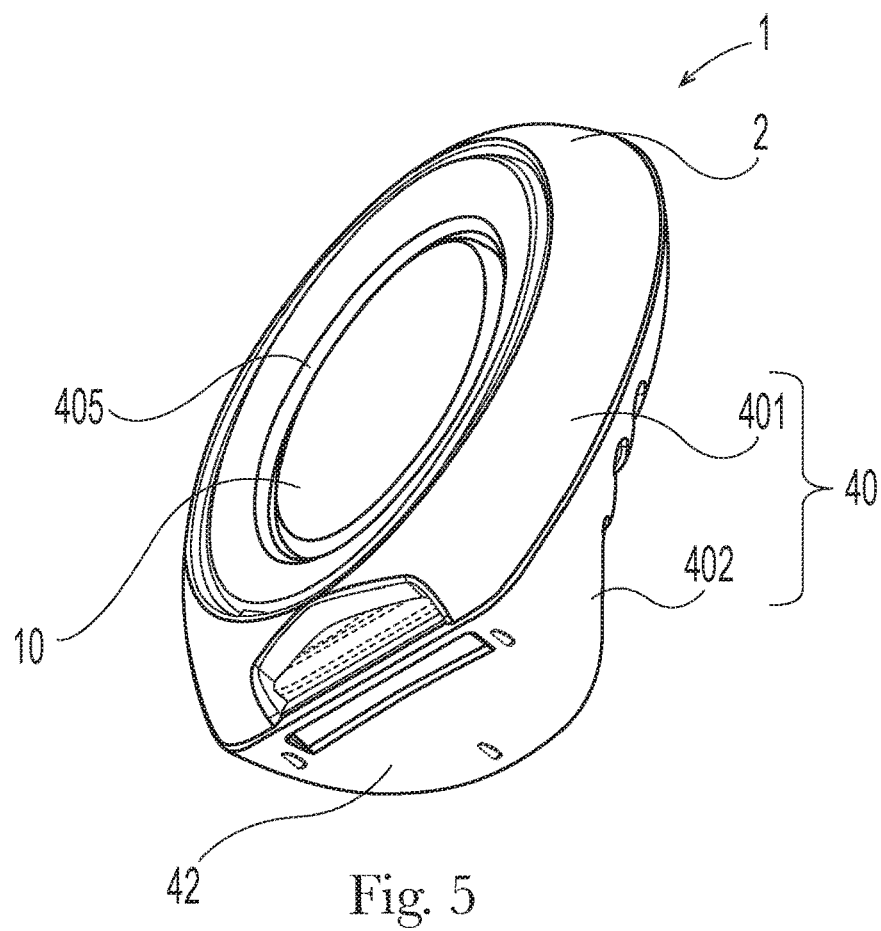
FIG. 5 is a front perspective view of a variation of an antibacterial air freshening product according to the present invention.
Figure 6:
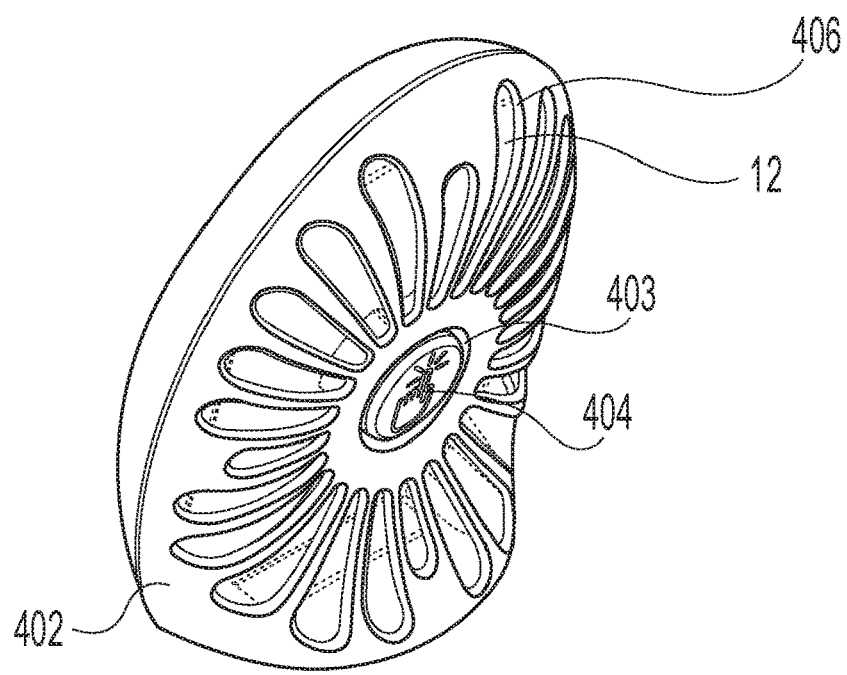
FIG. 6 is a rear perspective view of the product of FIG. 5.

FIG. 5 shows a front perspective view of a further exemplary example of a product 1 according to the present invention and FIG. 6 shows a rear perspective view of the product 1. FIG. 7 shows internal components of the product 1 of FIGS. 5 and 6. The product 1 of FIGS. 5, 6 and 7 comprise substantially the same features as the product 1 of FIG. 3 with additional components described as follows. Referring to FIGS. 5 and 6, the product 1 comprises a device 2 having a housing 40 having a front cover 401 and a rear frame 402, the front cover 401 and the rear frame 402 defining an interior space. The housing 40 may comprise a housing bottom surface 42 arranged for supporting the product 1 in a vertical orientation on a support in the interior environment.

The rear frame 402 is provided with a frame opening 403 (hereinafter "opening") located substantially in the centre of the rear frame 402. An actuator 404 movable relative to the housing 40 is provided for activating the product 1. The actuator 404 may be, for example, a push button 404 (hereinafter "button") disposed within the opening 403 and is movable with respect to the rear frame 402 for enabling a user to activate the product 1. The container 10 containing the composition 13 is located within the housing 40. The front cover 401 comprises a window 405 configured for displaying the container 10. The rear frame 402 comprises one or more apertures 406 spaced from the frame opening 403 for exposing an evaporative surface area of the membrane 12 to the environment.

When the composition 13 is a liquid volatile composition, the product 1 may comprise a rupturable substrate 14 sealably attached to and covering the reservoir 11 to prevent the composition 13 from being released until the product 1 is activated. The rupturable substrate 14 may be ruptured to release the composition 13 by actuating a rupture mechanism 61 positioned adjacent to the rupturable substrate 14. The rupture mechanism 61 comprises a movable member 62 movably attached to an outer frame 63 by a resilient member 64. The resilient member 64 may be formed of one or more springs 65. One or more rupture elements 66 are arranged within the rupture mechanism 61 to puncture holes in the rupturable substrate 14. The rupture element 66 may be a pin. Referring to FIG. 2 and FIG. 7, the membrane 12 may be sealably attached to a flange 67 located at the periphery 104 of the container 10. The membrane 12 encloses the container 10, the composition 13, the rupturable substrate 14, and the rupture mechanism 61. The membrane 12 may be configured to flex when a pressure or an actuation force is applied on the membrane 12 through the button 404. The membrane 12 of FIG. 7 may comprise an evaporative surface area of 27 cm$^2$.

Referring to FIG. 8, to activate the product 1, a user depresses the button 404 until it makes contact with the rupture mechanism 61 (through the deflection of the membrane 12 in a direction X towards the front end of the container), and the rupture elements 66 on the rupture mechanism 61 pierce the rupturable substrate 60. Once the rupturable substrate 14 is pierced, the composition 13 flows out of the container 10, wets the membrane 12 and is then delivered to the atmosphere surroundings through evaporation from the membrane 12. Specifically, wetting of the membrane 12 occurs when a liquid phase of the composition 13 comes into contact with and spreads on at least a part of the membrane first surface 121. The membrane 12 is configured to prevent the liquid phase of the composition 13 from flowing out of the membrane 12 but enables vaporization of a vapor phase of the composition 13 from the membrane second surface 122 so that the composition 13 is delivered to the environment.

The composition 13 may be delivered through a wick wherein the wick may be configured to have various different shapes and sizes. For example, the wick may have a cylindrical or an elongate cube shape. The wick may be defined by a length and a diameter or width, depending on the shape. The wick may have various lengths. For example, the length of the wick may be in the range of about 1 millimeter ("mm") to about 100 mm, or from about 5 mm to about 75 mm, or from about 10 mm to about 50 mm. The wick may have various diameters or widths. For example, diameter or width of the wick may be at least 1 mm, or at least 2 mm, or at least 3 mm, or at least 4 mm. A wick may exhibit a density. The wick density may be in the range of about 0.100 grams/cm$^3$ ("g/cc") to about 1.0 g/cc. A wick may comprise a porous or semi-porous substrate. The wick may be composed of various materials and methods of construction, including, but not limited to, bundled fibers which are compressed and/or formed into various shapes via overwrap (such as a non-woven sheet over-wrap) or made of sintered plastics such as PE, HDPE or other polyolefins. For example, the wick may be made from a plastic material such as polyethylene or a polyethylene blend.

Figure 9:
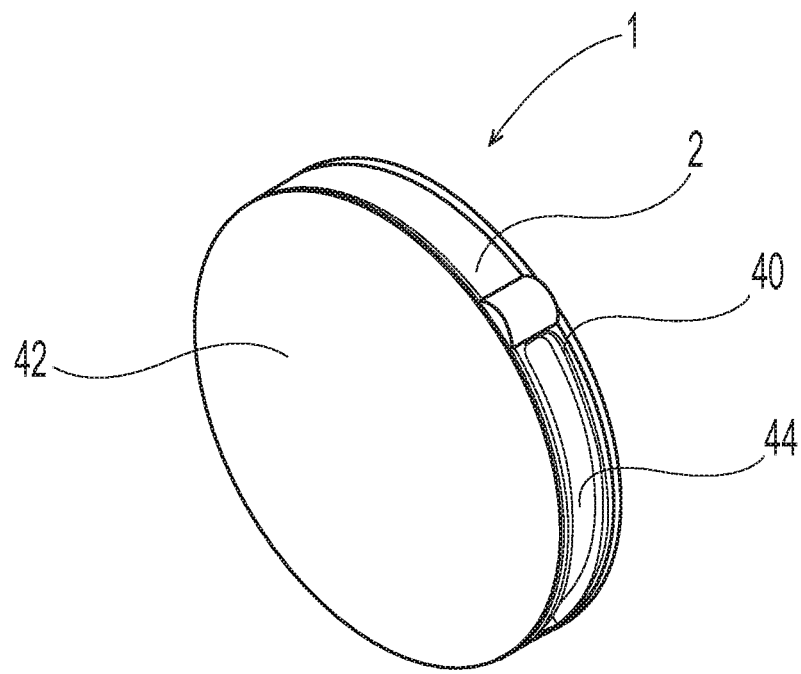
FIG. 9 is a variation of an antibacterial air freshening product according to the present invention.

FIG. 9 shows a variation of an air freshening product 1 according to the present invention. The product 1 of FIG. 9 comprises substantially the same components of the product 1 of FIG. 5 except for the device design. Specifically, the device 2 of FIG. 9 does not comprise a push button and has a different housing design from the housing 40 of the product 1 of FIG. 5 in that the housing 40 of FIG. 9 has a disc-like shape and a housing side opening 44 at a side of the housing 40 such that the composition 13 may be delivered from the side of the housing 40 through the housing side opening 44. An advantage of this configuration of an air freshening product 1 in an interior environment such as in a toilet environment is that if there is limited table-top space, the product 1 can be attached to a wall surface through a conventional vacuum suction cup so that the product 1 is proximal to the wall surface. Alternatively, the product 1 may be supported in a horizontal orientation on a support in the interior environment by placing on a housing bottom surface 42 of the housing 40.

The product 1 of the present invention can be configured for use in a variety of applications to deliver a freshening composition 13 to the atmosphere and/or a surface to prevent bacteria growth on the surface as long as the composition 13 is allowed to vaporize from the membrane 13 and come into contact with a surface having a bacterium deposited thereon.

Accordingly, the specific physical properties of the membrane 12 may be chosen based on the specific desired use of the product 1, designed to be activated by peeling off the vapor impermeable substrate 14 or by rupturing the vapor impermeable substrate 14. Membranes and vapor impermeable substrates designed to be releasably attached are known and will not be further described. Examples of suitable physical parameters of the membrane 13 and the vapor impermeable substrate 14 suitable for a product 1 designed to be activated by rupturing the vapor impermeable substrate 14 will be described hereinafter in the description.

The membrane 13 may be a microporous membrane and comprise an average pore size of about 0.01 to about 1 micron, about 0.01 to about 0.06 microns, from about 0.01 to about 0.05 microns, about 0.01 to about 0.04 microns, about 0.01 to about 0.03 microns, about 0.02 to about 0.04 microns, or about 0.02 microns. Further, the membrane 12 may be filled with any suitable filler and plasticizer known in the art. Fillers may include finely divided silica, clays, zeolites, carbonates, charcoals, and mixtures thereof. An example of a filled membrane is an ultra-high molecular weight polyethylene (UHMWPE) membrane filled with silica, such as those described in U.S. Pat. No. 7,498,369. Although any suitable fill material and weight percentage may be used, typical fill percentages for silica, may be between about 50% to about 80%, about 60% to about 80%, about 70% to about 80%, or about 70% to about 75% of the total weight of the membrane. Examples of suitable membrane thicknesses include, but are not limited to between about 0.01 mm to about 1 mm, between about 0.1 mm to 0.4 mm, about 0.15 mm to about 0.35 mm, or about 0.25 mm. Still further, an evaporative surface area of the membrane 12 may be about 2 cm² to about 100 cm², about 2 cm² to about 25 cm², about 10 cm² to about 50 cm², about 10 cm² to about 45 cm², about 10 cm² to about 35 cm², about 15 cm² to about 40 cm², about 15 cm² to about 35 cm², about 20 cm² to about 35 cm², about 30 cm² to about 35 cm², about 35 cm². The membrane 12 may comprise an evaporative surface area from 2 cm² to 80 cm², preferably from 5 cm² to 54 cm², more preferably from 6 cm² to 27 cm², even more preferably from 7 cm² to 10 cm².

The vapor impermeable substrate 14 may be made of any material that can be ruptured with a pre-determined applied force, with or without the presence of an element, such as rupture element, to aid in such rupture. In embodiments where the vapor impermeable substrate 40 is intended to contain the composition 13 when the product 1 is not in use, the vapor impermeable substrate 14 may be made from any suitable barrier material that reduces or prevents evaporation of the composition 13. Such materials may be impermeable to vapors and liquids. Suitable barrier materials for the vapor impermeable substrate 14 include, but are not limited to coated or uncoated films, such as polymeric films, webs, foils, and composite materials such as foil/polymeric film laminates. An example of a foil that may be used as a barrier material is a micron aluminum foil including a nitrocellulose protective lacquer, a polyurethane primer, and a 15 g/m2 polyethylene coating (Lidfoil 118-0092), available from Alcan Packaging. Suitable polymeric films include, but are not limited to, polyethylene terephtalate (PET) films, acrylonitrile copolymer barrier films such as, for example, those sold under the tradename Barex® by INOES, ethylene vinyl alcohol films, and combinations thereof. It is also contemplated that coated barrier films may be utilized as the vapor impermeable substrate 14. Such coated barrier films include, but are not limited to, metallized PET, metalized polypropylene, silica or alumina coated film.

The following examples are intended to more fully illustrate the present invention and are not to be construed as limitations of the present invention since many variations thereof are possible without departing from the scope of the present invention. All parts, percentages and ratios used herein are expressed as percent weight unless otherwise specified.

EXAMPLES

Test equipment/materials and test freshening compositions are first described under Materials, then Test Methods are provided, and lastly results are discussed. Data is provided demonstrating the freshening compositions of the present invention having improved antibacterial efficacy on a surface comprising a permeable material in an interior environment. Equipment and materials used in the Test Methods described hereinafter are listed in Table 4 below. The formulations of inventive compositions are provided in Table 5 below. The compositions are prepared using conventional methods.

In the following Examples, the freshening product evaluated is designed as a consumer product, such as a toilet deodorizer, for evaporating a freshening composition in a toilet to deliver a variety of benefits such as bacteria growth prevention on permeable inanimate surfaces, freshening, malodor removal or scenting of air in the toilet. Accordingly, the equipment, materials have been designed to mimic conditions inside a toilet. However, it is contemplated that the product may be configured for use in a variety of applications to deliver a freshening composition to provide the benefits in interior environments such as furniture for storage of personal items in household and commercial establishments, and the product may include but is not limited to consumer products, such as, for example air freshening products, air fresheners, deodorizers or the like. Therefore, in a different application whereby the interior environment has a different volume such as a shoe cabinet, it will be appreciated that the equipment, materials and methods can be modified accordingly to demonstrate the freshening compositions of the present invention having improved antibacterial efficacy on a surface comprising a permeable material in an interior environment of a different volume.

Materials

TABLE 4

Equipment/Materials

| Component | Example |
|---|---|
| Space to simulate the environment of a bathroom containing a toilet (hereinafter "toilet") | Test Chamber (Interior Volume of 345 liters, Interior dimensions - 39.25 (Width) × 25 (Depth) × 21.5 (Height) inches) |
| Bacteria Species as a representative sample of a commonly found bacteria species in the toilet (hereinafter "Bacterium") | |
| Bacterium Sample 1 | *S. aureus* (gram-positive bacteria) |
| Bacterium Sample 2 | *Enterococcus hirae* (gram-positive bacteria) |
| Bacterium Sample 3 | *K pneumoniae* (gram-negative bacteria) |
| Bacterium Sample 4 | *P mirabilis* (gram-negative bacteria) |
| Bacterium Sample 5 | *E coli* (gram-negative bacteria) |
| Medium used for preparation of bacterial solution | Nutrient Broth |
| Neutralize the volatile aldehydes deposited on the permeable material for evaluation | Mod. Tween Letheen B (MLBT) |
| Permeable Material A | Sterile 2 cm × 2 cm - floor mat (cotton) |
| Permeable Material B | Sterile 2 cm × 2 cm - vinyl cushion material |
| Permeable Material C | Sterile 2 cm × 2 cm - Kanakin (also known as cotton, Kanakin is the Japanese term for the cotton) |
| Permeable Material D | Sterile 2 cm × 2 cm - terry towel |
| Inventive Air Freshening Product 1 | Device similar in configuration to Device 2 of FIG. 5 and containing 6 ml of Inventive Composition 1 Delivery Member = Membrane having an evaporative surface area of 27 cm2 |

TABLE 4-continued

| Equipment/Materials | |
|---|---|
| Component | Example |
| Inventive Air Freshening Product 2 | Device similar in configuration to Device 2 of FIG. 5 and containing 6 ml of Inventive Composition 2<br>Delivery Member = Membrane having an evaporative surface area of 27 cm2 |
| Inventive Air Freshening Product 3 | Device similar in configuration to Device 2 of FIG. 5 and containing 6 ml of Inventive Composition 3<br>Delivery Member = Membrane having an evaporative surface area of 27 cm2 |
| Inventive Air Freshening Product 4 | Device similar in configuration to Device 2 of FIG. 5 and containing 6 ml of Inventive Composition 4<br>Delivery Member = Membrane having an evaporative surface area of 27 cm2 |

Table 5 describes four freshening compositions which are evaluated. Inventive Compositions 1, 2, 3 are inventive compositions containing a volatile aldehyde mixture of C5 to C8 Sunbranched unsubstituted linear alkenal ((E)-2-Hexen-1-al CAS No. 6728-26-3 as an example) and a C9 to C14 unbranched unsubstituted linear alkenal ((E)-2-decen-1-al CAS No. 3913-81-3 as an example) in different levels, and weight ratio of 1:1.

Inventive Composition 4 is an inventive composition containing a volatile aldehyde mixture of a C5 to C8 unbranched unsubstituted linear alkenal ((E)-2-Hexen-1-al as an example) and a C9 to C14 unbranched unsubstituted linear alkenal ((E)-4-decen-1-al as an example) in different levels, and a weight ratio of 1:1.

TABLE 5

| Formulations of Inventive Compositions | | | | | |
|---|---|---|---|---|---|
| Ingredients (by weight of the composition (wt %)) | | Inventive Composition | Inventive Composition | Inventive Composition | Inventive Composition |
| CAS No. | IUPAC Name | 1 | 2 | 3 | 4 |
| 6728-26-3 | (E)-2-Hexen-1-al | 0.25% | 1% | 3% | 1.5% |
| 3913-81-3 | (E)-2-Decen-1-al | 0.25% | 1% | 3% | — |
| 65405-70-1 | 4-decenal-1-al | — | — | — | 1.5% |
| — | Perfume Accord 1* | — | 98% | 94% | 97% |
| — | Perfume Accord 2* | 99.5% | — | — | — |
| Weight Percentage Total: | | 100 | 100 | 100 | |

*Accord ingredients are not disclosed by the manufacturer.

Test Method(s)
A. JIS L1902:2015 Textiles—Determination of Antibacterial Activity and Efficacy of Textile Products (Hereinafter "JIS L 1902 Method")

The Japanese Industrial Standards (JIS) L 1902 method titled "Determination of antibacterial activity and efficacy of textile products" is a known JIS method used for testing antibacterial activity of fabrics and textiles that have been treated with antimicrobial agents to prevent microbial growth over a predetermined time period. Within JIS L 1902 method, there are 3 main types of tests:
1) JIS L 1902 Absorption Method—Quantitative Test
2) JIS L 1902 Printing Method—Quantitative Test
3) JIS L 1902 Halo Method—Qualitative Test As JIS L 1902 method can be readily purchased online at for example, https://webdesk.jsa.or.jp/books/W11M0070/index, the JIS L 1902 method is not reproduced here. The JIS L 1902 Absorption Method is used and detailed in one of the steps of the P&G Test Method for Evaluating Antibacterial Efficacy of Air Freshening Product described hereinafter.

B. P&G Test Method for Evaluating Antibacterial Efficacy of Air Freshening Product This test method is to evaluate an antibacterial efficacy of an air freshening product in reducing bacteria growth in an interior environment such as for example a bathroom containing a toilet.

The test method is performed in the Test Chamber under the following test conditions:
  a) Average air exchange range is 1-2 ACH
  b) Average Temperature—23 degrees Celsius+/−0.1 degrees Celsius
  c) Average % Relative Humidity of 60%+/−5%.

The steps for performing the above test method include:
1. Place 0.4 grams of a Permeable Material (e.g. Permeable Material A) in an empty petri dish in the Test Chamber and incubate for 24 to 72 hours at the above conditions to obtain Control Untreated Permeable Material A0.
2. Place 0.4 grams of Permeable Material A in an empty petri dish in the Test Chamber with Inventive Air Freshener Product 1 and incubate for 24 to 72 hours at the above conditions to obtain Treated Permeable Material A1. Repeat Step 1 with Inventive Air Freshener Product 1, 2, 3 to obtain Treated Permeable Material A2, Treated Permeable Material A3, Treated Permeable Material A4.
3. Transfer Control Untreated Permeable Material A0, Treated Permeable Material A1, Treated Permeable Material A2, Treated Permeable Material A3 and Treated Permeable Material A4 into individual 30 ml glass vials such that each glass vial contains only one permeable material.

4. Each of the Untreated Permeable Material A0, Treated Permeable Materials 1, 2, 3 and 4 in the glass vial is evaluated according to JIS L1902 Absorption Test described hereinafter using Bacterium Sample 1, Bacterium Sample 2, Bacterium Sample 3, Bacterium Sample 4 and Bacterium Sample 5.

5. Perform the following steps according to JIS L 1902 Absorption Test:
   (i) Subculture each of the Bacterium Sample 1, 2, 3, 4, 5 on individual TSA plates at 35° C. overnight for 18-24 hours to form 24-hour culture plates.
   (ii) Take a single colony on each of the 24-hour culture plates from (i) above and suspend in 20 ml of Nutrient Broth in Falcon® 50 ml tube, and incubate overnight with shaking at 120 rpm at 37° C. to form an overnight culture.
   (iii) Transfer 0.2 ml of the overnight culture from (ii) above to another 20 ml of Nutrient Broth (room temp.) in Falcon® 50 ml tube, and incubate 3 hours with shaking at 120 rpm at 37° C. to form a 3 hours culture.
   (iv) Prepare 5% Nutrient Broth solution by adding 0.5 ml of sterile Nutrient Broth in 9.5 ml sterile water.
   (v) Dilute the 3 hours culture from (iii) above using 5% nutrient broth solution from (iv) above to make an inoculum which has approximately $1 \times 10^5$ cfu/ml.
   (vi) Inoculate 0.2 ml of the inoculum onto each of Control Treated Permeable Material, Inventive Treated Permeable Material 1, Inventive Treated Permeable Material 2, and Inventive Treated Permeable Material 3 contained in the vials to control an initial number of bacteria.
   (vii) After inoculation, cover each of the vials containing the Control Untreated Permeable Material A0, Treated Permeable Materials A1, A2, A3, A4 with a sterile plastic film (2 cm by 2 cm) when tested using vinyl cushion.
   (viii) Incubate the vials containing the Control Untreated Permeable Material A0 and Treated Permeable Material A1, A2, A3, A4 for 18 to 24 hours at 37° C.
   (ix) Add 20 ml of MLBT into each of the vials of step (viii) to neutralize perfume active on materials and shake with a vortex mixer for 30 seconds.
   (x) Serially dilute bacteria population in (ix) using saline to get reduced and put reduced size of bacterial population on plate with TSA.
   (xi) Count colonies on plate to obtain a number of bacteria at a start time ("Start Time").
   (xii) Incubate plates at 37° C. overnight for 24 to 48 hours to reach visually detectable amount.
   (xiii) Count colonies that appear on each TSA plate by observing with the naked eye at the end of 18 hours from the Start Time to obtain a number of bacteria of Untreated Permeable Material and a number of bacteria of Treated Permeable Material.

An antibacterial activity value at a specific time point T (for example after 18 hours) may be determined according to the following equation:

Antibacterial Activity value at $T$=Number of bacteria of Untreated Permeable Material (log cfu at $T$)–Number of bacteria of Treated Permeable Material (log cfu at $T$)

The above Untreated Permeable Material and the Treated Permeable Material are of the same material type. An antibacterial activity value corresponds to a measurable value of how effective a specific treated permeable material is in preventing bacteria growth relative to an untreated permeable material. Accordingly, the higher an antibacterial activity value correlates to a higher efficacy of the treated permeable material in preventing bacteria growth as shown in a reduced number of bacteria counted on the treated permeable material relative to a number of bacteria counted on the untreated permeable material at the end of a same specific period of time.

Example I

Inventive Air Freshening Products 1, 2, 3 and 4 are evaluated according to the P&G Test Method for Evaluating Antibacterial Efficacy of Air Freshening Product described hereinbefore under Test Methods based on Bacterium Sample and Permeable Material C (Kanakin).

Figure 10:
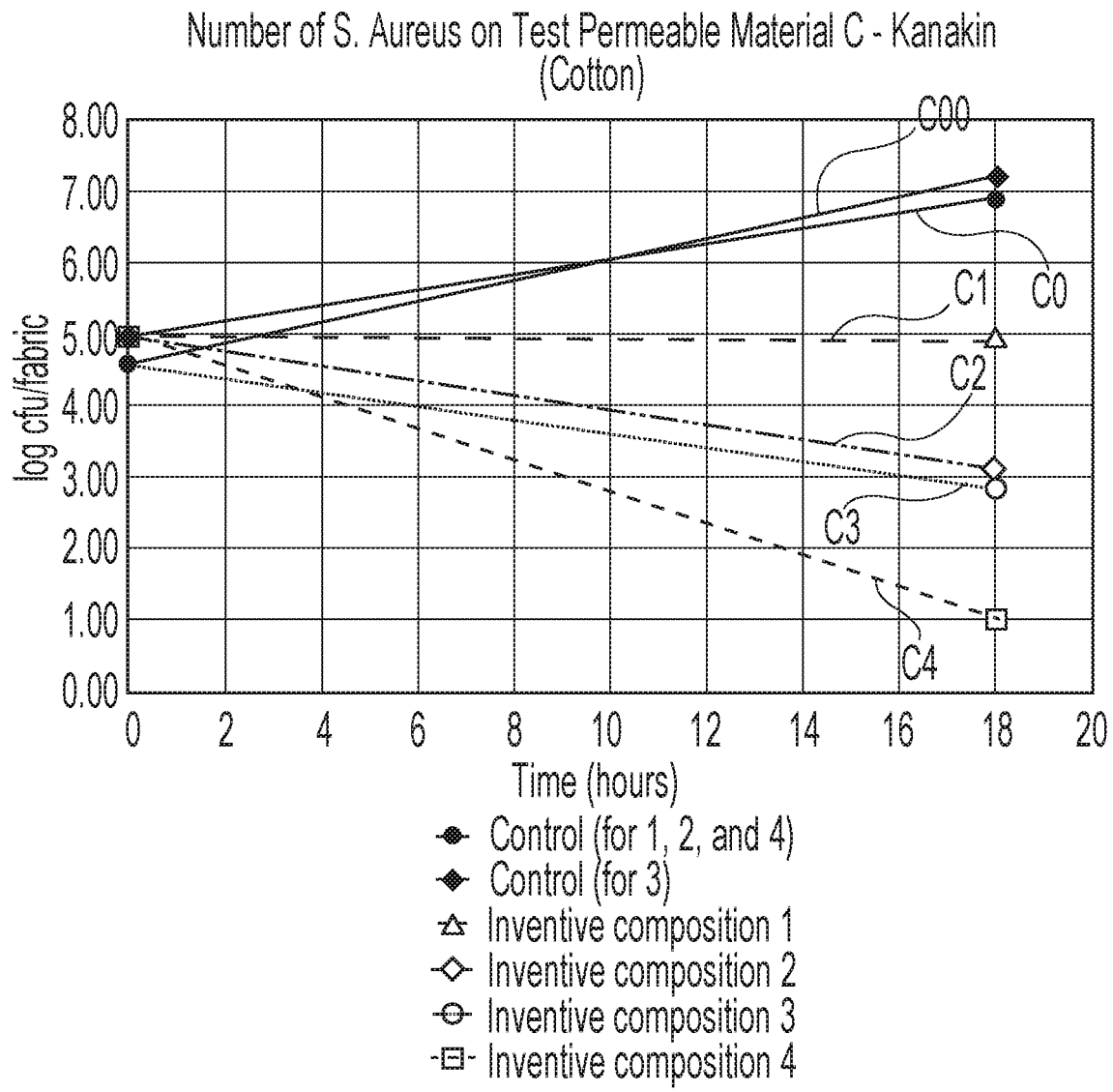
FIG. 10 is a graph plotting numbers of bacteria of an untreated permeable material and the same permeable material treated with Inventive Air Freshening Products 1, 2, 3 and 4 against gram-positive bacterium (S. aureus) as a function of time.

Table 6 below show antibacterial activity values of Permeable Material C treated with Inventive Air Freshening Products 1, 2, 3 and 4 respectively and Untreated Permeable Material C measured at a time point of 18 hours. FIG. 10 is a corresponding graph of Table 6. Table 6 also includes an antibacterial activity value of Permeable Material C treated with the Inventive Air Freshening Products 1, 2, 4 relative to the Untreated Permeable Material C0 and an antibacterial activity value of Permeable Material C treated with Inventive Air Freshening Product 3 relative to the Untreated Permeable Material C00.

TABLE 6

Antibacterial Activity Value of Permeable Material C (Kanakin) treated with Inventive Compositions 1, 2, 3, 4 against Bacterium Sample 1 (*S. aureus*)

| Samples | Number of bacteria Start Time 0 Hours | Number of bacteria at 18 hours after Start Time | Antibacterial (AB)Activity Value |
|---|---|---|---|
| Untreated Permeable Material C0 (Control for Treated Permeable Material C1, C2 and C4) ("C0") | 4.98 | 6.90 | Ref |
| Untreated Permeable Material C00 (Control for Treated Permeable Material C3) ("C00") | 4.59 | 7.21 | Ref |
| Treated Permeable Material C1 (Inventive Composition 1) ("C1") | 4.98 | 4.91 | 1.98 |
| Treated Permeable Material C2 (Inventive Composition 2) ("C2") | 4.98 | 3.11 | 3.79 |

TABLE 6-continued

Antibacterial Activity Value of Permeable Material C (Kanakin) treated with
Inventive Compositions 1, 2, 3, 4 against Bacterium Sample 1 (S. aureus)

| Samples | Number of bacteria Start Time 0 Hours | Number of bacteria at 18 hours after Start Time | Antibacterial (AB)Activity Value |
|---|---|---|---|
| Treated Permeable Material C3 (Inventive Composition 3) ("C3") | 4.39 | 2.83 | 4.07 |
| Treated Permeable Material C4 (Inventive Composition 4) ("C4") | 4.98 | 1.00 | 5.90 |

Referring to FIG. 10 and Table 6, all treated Permeable Materials C1-C4 with Inventive Compositions 1, 2, 3, 4 respectively having a volatile aldehyde mixture of C5 to C8 unbranched unsubstituted linear alkenal (for example, (E)-2-Hexen-1-al) and C9 to C14 unbranched unsubstituted linear alkenal (for example, 2-Decen-1-al or 4-Decen-1-al) have improved antibacterial activity values relative to the Untreated Permeable Material C0 and Untreated Permeable Material COO.

In particular, Inventive Composition 3 having a volatile aldehyde mixture of C5 to C8 unbranched unsubstituted linear alkenal (for example, (E)-2-Hexen-1-al) in an amount of 3% and C9 to C14 unbranched unsubstituted linear alkenal (for example, (E)2-Decen-1-al) in an amount of 3% enables a higher antibacterial activity value (4.39) relative to Inventive Composition 1 having an antibacterial activity value of 1.98 (having the same volatile aldehyde mixture, (E)-2-Hexen-1-al in a lower amount of 1%, (E)-2-decenal in a lower amount of 1%).

Inventive Composition 4 having a volatile aldehyde mixture of C5 to C8 unbranched unsubstituted linear alkenal (for example, (E)-2-Hexen-1-al) and C9 to C14 unbranched unsubstituted linear alkenal (for example, 4-Decen-1-al) has the highest antibacterial activity value of 5.90.

Referring to FIG. 10, each of the plots corresponding to number of bacteria of the Treated Permeable Material C1, C2, C3, C4 (shown in dotted lines) show a decrease in the activity of Bacterium Sample 1 (S. aureus) over a period of time, specifically from the start of the test at 0 hours to 18 hours, i.e. the end of the test. On the other hand, all the Control Untreated Permeable Material C0, COO.

Example II

Inventive Air Freshening Product 3 is evaluated according to the P&G Test Method for Evaluating Antibacterial Efficacy of Air Freshening Product described hereinbefore under Test Methods based on Bacterium Sample 1 (S. aureus) and the Test Permeable Materials described below.

Figure 11:
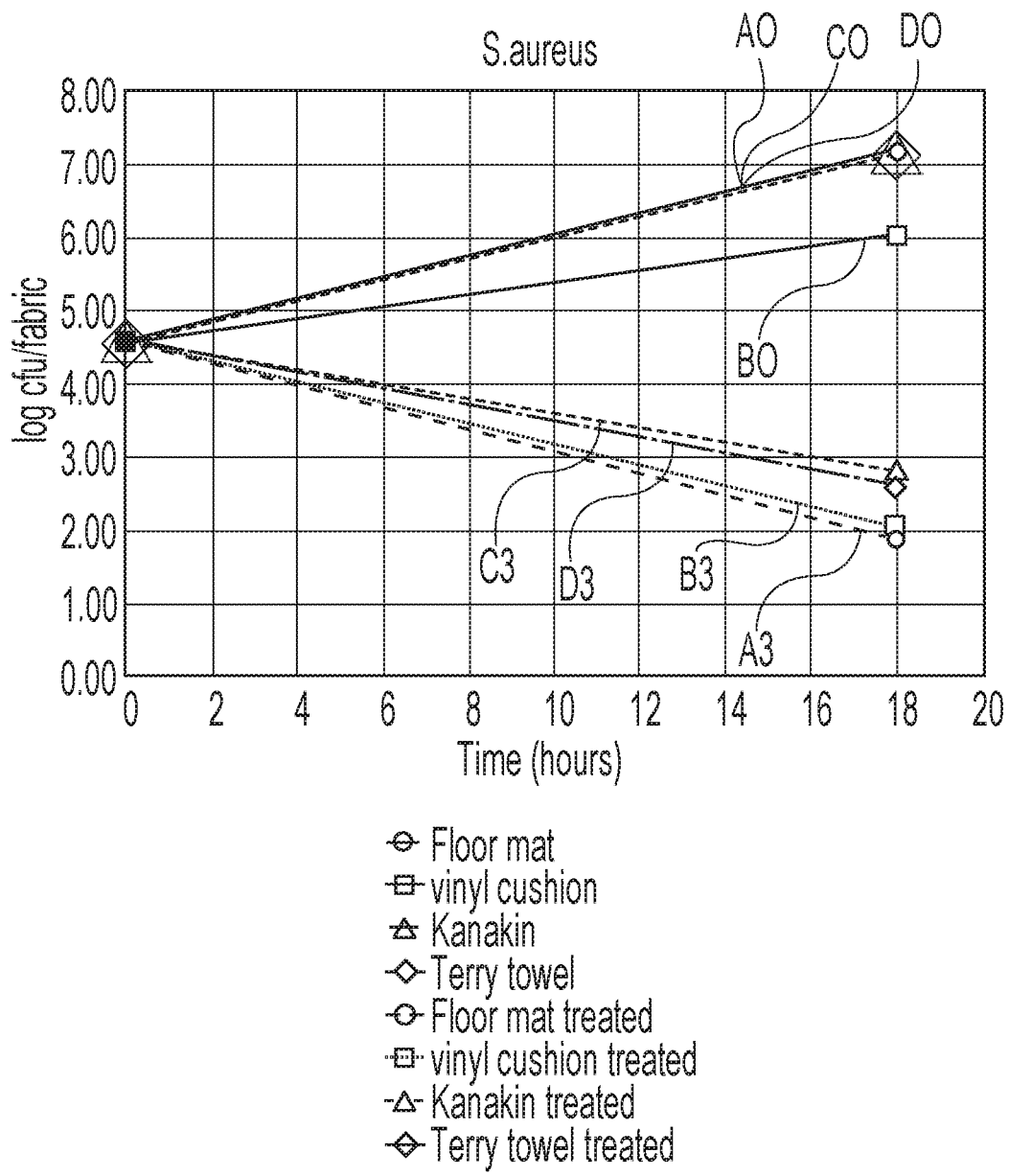
FIG. 11 is a graph plotting numbers of bacteria of different untreated test permeable materials and different test permeable materials treated with Inventive Air Freshening Product 3 against gram-positive bacterium (E. hirae) as a function of time.

Table 7 below shows antibacterial activity value of Inventive Air Freshener Product 3 with Inventive Composition 3 having a mixture of 3% of C5 to C8 unbranched unsubstituted linear alkenal and 3% of C9 to C14 unbranched unsubstituted linear alkenal by weight of the composition. Inventive Composition 3 is applied to different Test Permeable Materials (named as Treated Permeable Material A3, B3, C3 and D3 as shown below in Table 7) and assessed for antibacterial efficacy against Bacterium Sample 1 (S. aureus). FIG. 11 is a corresponding graph of Table 7.

TABLE 7

Antibacterial Activity Value of Different Permeable Materials treated
with Inventive Composition 3 against Bacterium Sample 1 (S. aureus)

| Samples | Number of bacteria at 0 hours ("Start Time") | Number of bacteria at 18 hours after Start Time | Antibacterial (AB)Activity Value |
|---|---|---|---|
| Untreated Permeable Material A0 | 4.59 | 7.19 | Ref |
| Untreated Permeable Material B0 | 4.59 | 6.06 | Ref |
| Untreated Permeable Material C0 | 4.59 | 7.21 | Ref |
| Untreated Permeable Material D0 | 4.59 | 7.16 | Ref |
| Treated Permeable Material A3 | 4.59 | 1.90 | 5.29 |
| Treated Permeable Material B3 | 4.59 | 2.08 | 3.98 |
| Treated Permeable Material C3 | 4.59 | 2.83 | 4.38 |
| Treated Permeable Material D3 | 4.59 | 2.63 | 4.52 |

The results in FIG. 11 and Table 7 show an air freshening composition having the combination of trans-2-hexenal and trans-2-decenal in a level of 3% can be effectively vaporized and deposited on each of the different Permeable Materials to inhibit the growth of bacteria on each Permeable Material and achieve an antibacterial activity value of at least 3 for any one of the Treated Permeable Materials.

Example III

Inventive Air Freshening Product 3 is evaluated according to the P&G Test Method for Evaluating Antibacterial Efficacy of Air Freshening Product described hereinbefore under Test Methods based on the Bacterium Sample 2 (E. hirae) and the Test Permeable Materials described below.

Figure 12:
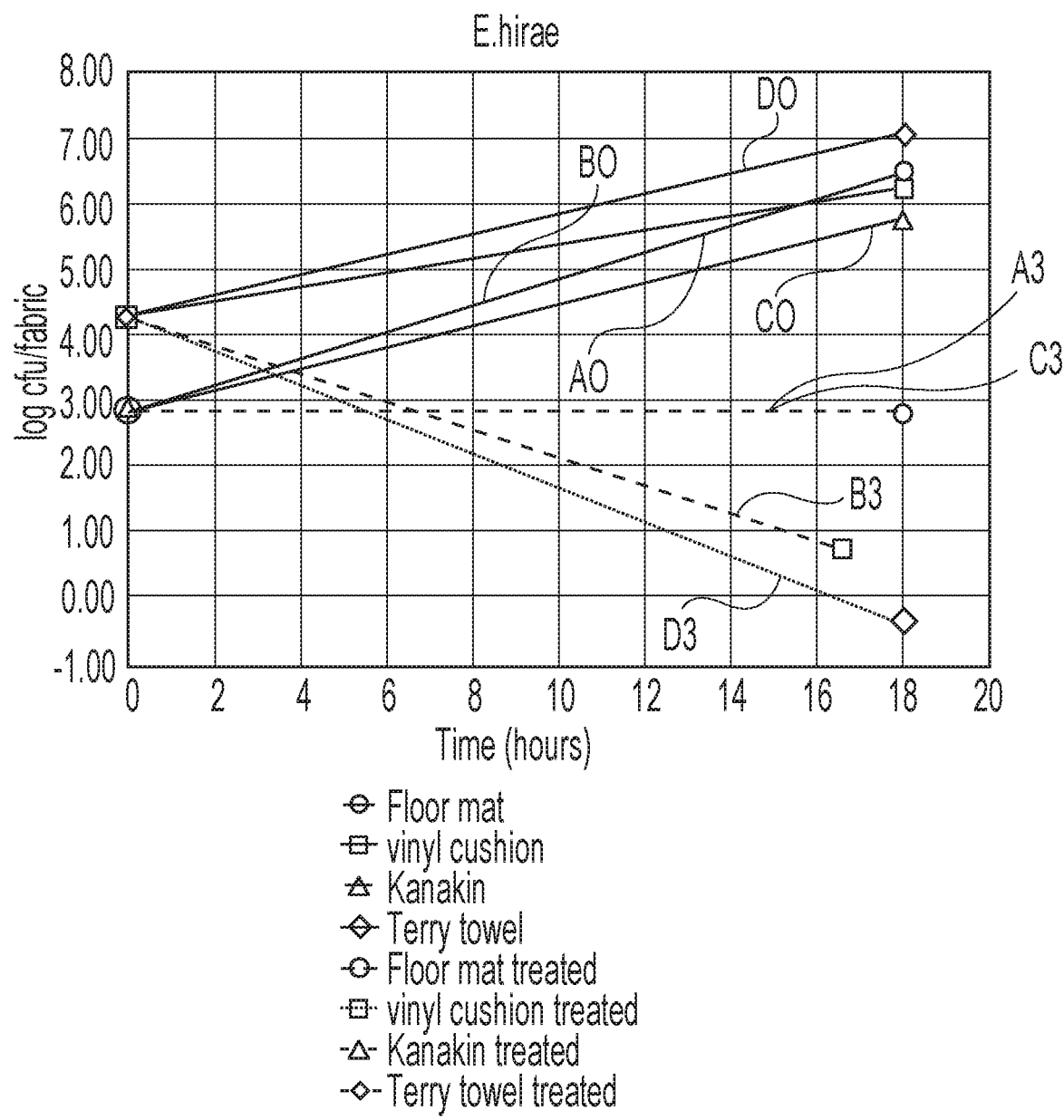
FIG. 12 is a graph plotting numbers of bacteria of different untreated test permeable materials and different test permeable materials treated with Inventive Air Freshening Product 3 against gram-positive bacterium (S. aureus) as a function of time.

Table 8 below shows antibacterial activity value of Inventive Air Freshener Product 3 with Inventive Composition 3 having a mixture of 3% of C to C8 unbranched unsubstituted linear alkenal and 3% of C9 to C14 unbranched unsubstituted linear alkenal by weight of the composition. Inventive Composition 3 is applied to different Test Permeable Materials as shown below and assessed for antibacterial efficacy against Bacterium Sample 2 (hirae). FIG. 12 is a corresponding graph of Table 8.

TABLE 8

Antibacterial Activity Value of Different Permeable Materials treated
with Inventive Composition 3 against Bacterium 2 (*E. hirae*)

| Samples | Number of bacteria at 0 hours ("Start Time") | Number of bacteria at 18 hours after Start Time | Antibacterial (AB)Activity Value |
|---|---|---|---|
| Untreated Permeable Material A0 | 2.90 | 6.46 | Ref |
| Untreated Permeable Material B0 | 4.29 | 6.28 | Ref |
| Untreated Permeable Material C0 | 2.90 | 5.78 | Ref |
| Untreated Permeable Material D0 | 4.29 | 7.05 | Ref |
| Treated Permeable Material A3 | 2.90 | 2.71 | 3.75 |
| Treated Permeable Material B3 | 4.29 | 0.48 | 5.80 |
| Treated Permeable Material C3 | 2.90 | 2.74 | 3.04 |
| Treated Permeable Material D3 | 4.29 | −0.30 | 7.35 |

The results in FIG. 12 and Table 8 above show an air freshening composition having the combination of trans-2-hexenal and trans-2-decenal in a level of 3% can be effectively vaporized and deposited on each of the different Permeable Materials to inhibit the growth of bacteria on each Permeable Material and achieve an antibacterial activity value of at least 3 for any one of the Treated Permeable Materials.

Example IV

Inventive Air Freshening Product 3 is evaluated according to the P&G Test Method for Evaluating Antibacterial Efficacy of Air Freshening Product described hereinbefore under Test Methods based on the Bacterium Sample 3 (*P. mirabilis*) and the Test Permeable Materials described below.

Figure 13:
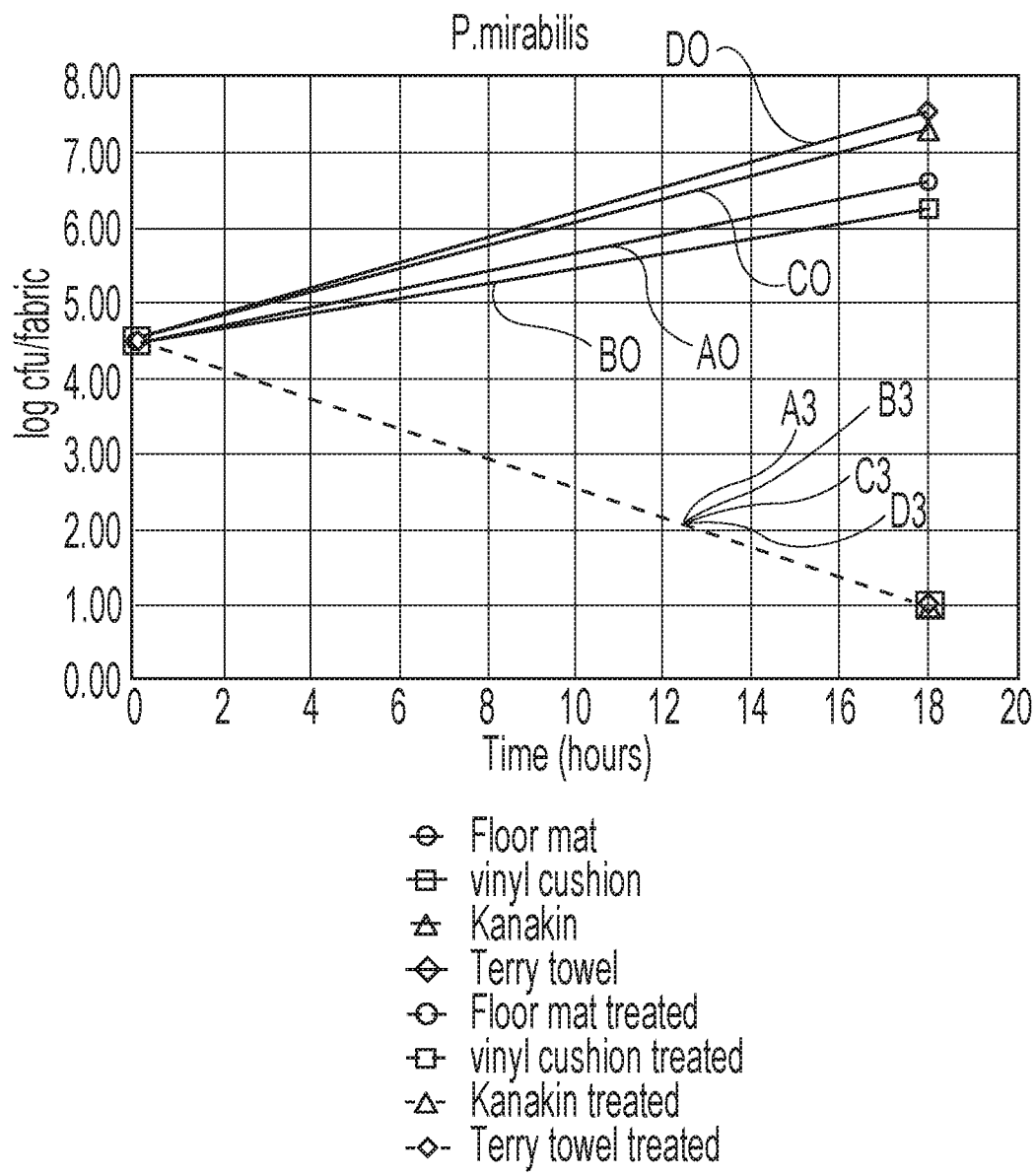
FIG. 13 is a graph plotting numbers of bacteria of different untreated test permeable materials and different test permeable materials treated with Inventive Air Freshening Product 3 against gram-negative bacterium (P. mirabilis) as a function of time.

Table 9 below shows antibacterial activity value of Inventive Air Freshener Product 3 with Inventive Composition 3 having a mixture of 3% of C5 to C8 unbranched unsubstituted linear alkenal and 3% of C9 to C14 unbranched unsubstituted linear alkenal by weight of the composition. Inventive Composition 3 is applied to different Test Permeable Materials as shown below and assessed for antibacterial efficacy against Bacterium Sample 3 (*P. mirabilis*). FIG. 13 is a corresponding graph of Table 9.

TABLE 9

Antibacterial Activity Value of Different Permeable Materials treated with
Inventive Composition 3 against Bacterium Sample 3 (*P. mirabilis*)

| Samples | Number of bacteria at 0 hours ("Start Time") | Number of bacteria at 18 hours after Start Time | Antibacterial (AB)Activity Value |
|---|---|---|---|
| Untreated Permeable Material A0 | 4.52 | 6.62 | Ref |
| Untreated Permeable Material B0 | 4.52 | 6.27 | Ref |
| Untreated Permeable Material C0 | 4.52 | 7.32 | Ref |
| Untreated Permeable Material D0 | 4.52 | 7.53 | Ref |
| Treated Permeable Material A3 | 4.52 | 1.00 | 5.62 |
| Treated Permeable Material B3 | 4.52 | 1.00 | 5.27 |
| Treated Permeable Material C3 | 4.52 | 1.00 | 6.32 |
| Treated Permeable Material D3 | 4.52 | 1.00 | 6.53 |

The above results in Table 9 show that an inventive freshening composition comprising trans-2-hexenal and trans-2-decenal in a respective level of 3% by weight of the composition demonstrate an antibacterial activity value of at least 5 on each of the different test permeable materials for Bacterium Sample 3 (*P. mirabilis*). The results of Treated Permeable Material D3 has the highest antibacterial activity value (6.53) relative to the Untreated Permeable Material D0.

Referring to FIG. 13, each of the profiles corresponding to Treated Permeable Materials A3, B3, C3 and D3 show a substantially similar rate of decreased bacterial activity of Bacterium Sample 3 (*P. mirabilis*) relative to the respective Untreated Permeable Materials.

Example V

Inventive Air Freshening Product 3 is evaluated according to the P&G Test Method for Evaluating Antibacterial Efficacy of Air Freshening Product described hereinbefore under Test Methods based on the Bacterium Sample 4 (*K. pneumoniae*) and the Test Permeable Materials described below.

Figure 14:
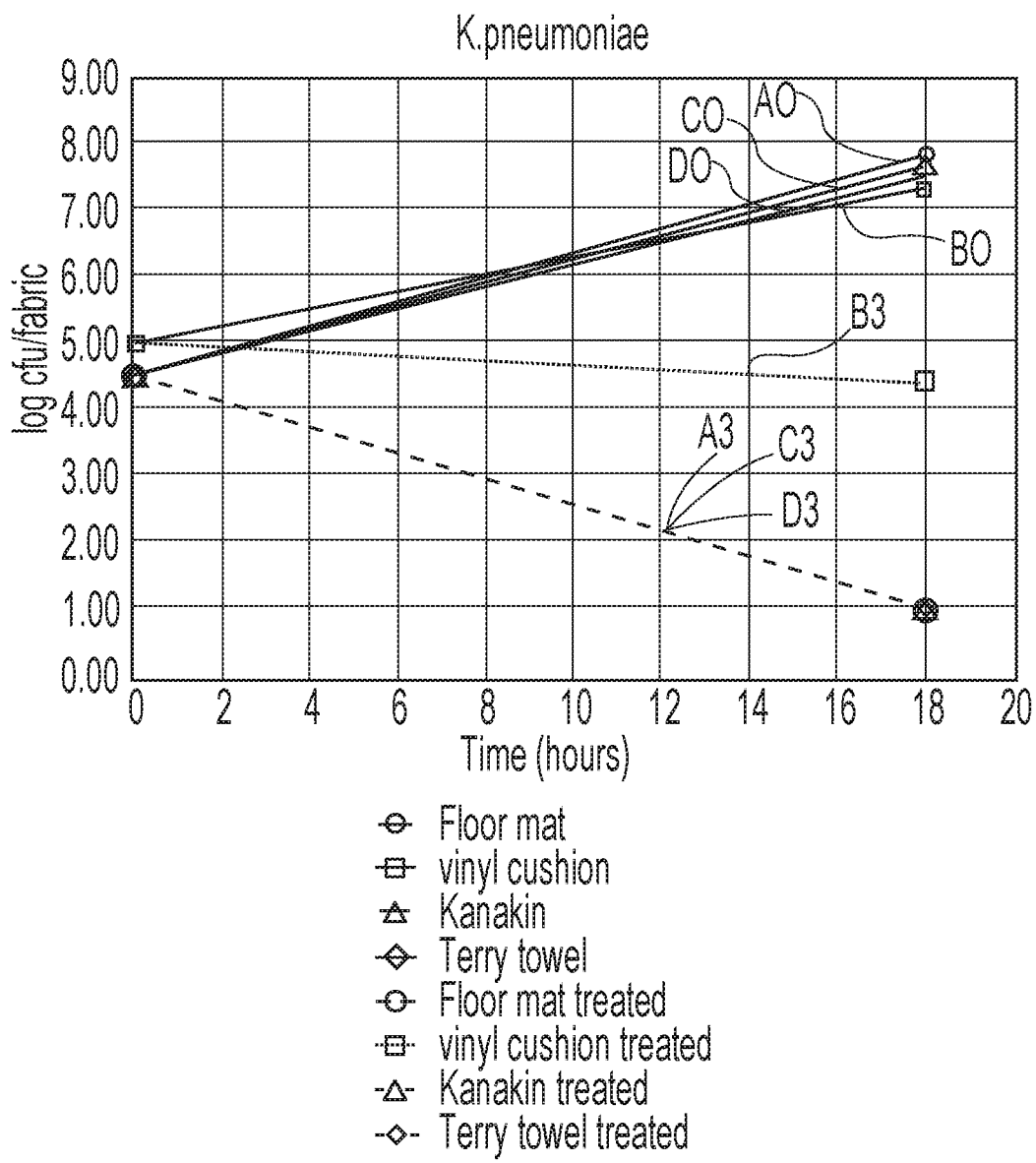
FIG. 14 is a graph plotting numbers of bacteria of different untreated test permeable materials and different test permeable materials treated with Inventive Air Freshening Product 3 against gram-negative bacterium (K. pneumoniae) as a function of time.

Table 10 below shows antibacterial activity value of Inventive Air Freshener Product 3 with Inventive Composition 3 having a mixture of 3% of C5 to C8 unbranched unsubstituted linear alkenal and 3% of C9 to C14 unbranched unsubstituted linear alkenal by weight of the composition. Inventive Composition 3 is applied to different Test Permeable Materials as shown below and assessed for antibacterial efficacy against Bacterium Sample 4 (*K. pneumoniae*). FIG. 14 is a corresponding graph of Table 10.

TABLE 10

Antibacterial Activity Value of Different Permeable Materials treated with Inventive Composition 3 against Bacterium Sample 4 (*K. pneumoniae*)

| Samples | Number of bacteria at 0 hours ("Start Time") | Number of bacteria at 18 hours after Start Time | Antibacterial (AB)Activity Value |
|---|---|---|---|
| Untreated Permeable Material A0 | 4.49 | 7.80 | Ref |
| Untreated Permeable Material B0 | 4.97 | 7.28 | Ref |
| Untreated Permeable Material C0 | 4.49 | 7.63 | Ref |
| Untreated Permeable Material D0 | 4.49 | 7.48 | Ref |
| Treated Permeable Material A3 | 4.49 | 1.00 | 6.80 |
| Treated Permeable Material B3 | 4.97 | 4.37 | 2.91 |
| Treated Permeable Material C3 | 4.49 | 1.00 | 6.63 |
| Treated Permeable Material D3 | 4.49 | 1.00 | 6.48 |

The above results show that an inventive freshening composition comprising trans-2-hexenal and trans-2-decenal in a respective level of 3% by weight of the composition demonstrate an antibacterial activity value of at least 2 on each of the different test permeable materials for Bacterium Sample 4 (*K. pneumoniae*).

Example VI

Inventive Air Freshening Product 3 is evaluated according to the P&G Test Method for Evaluating Antibacterial Efficacy of Air Freshening Product described hereinbefore under Test Methods based on the Bacterium Sample 5 (*E. coli*) and the Test Permeable Materials described below.

Figure 15:
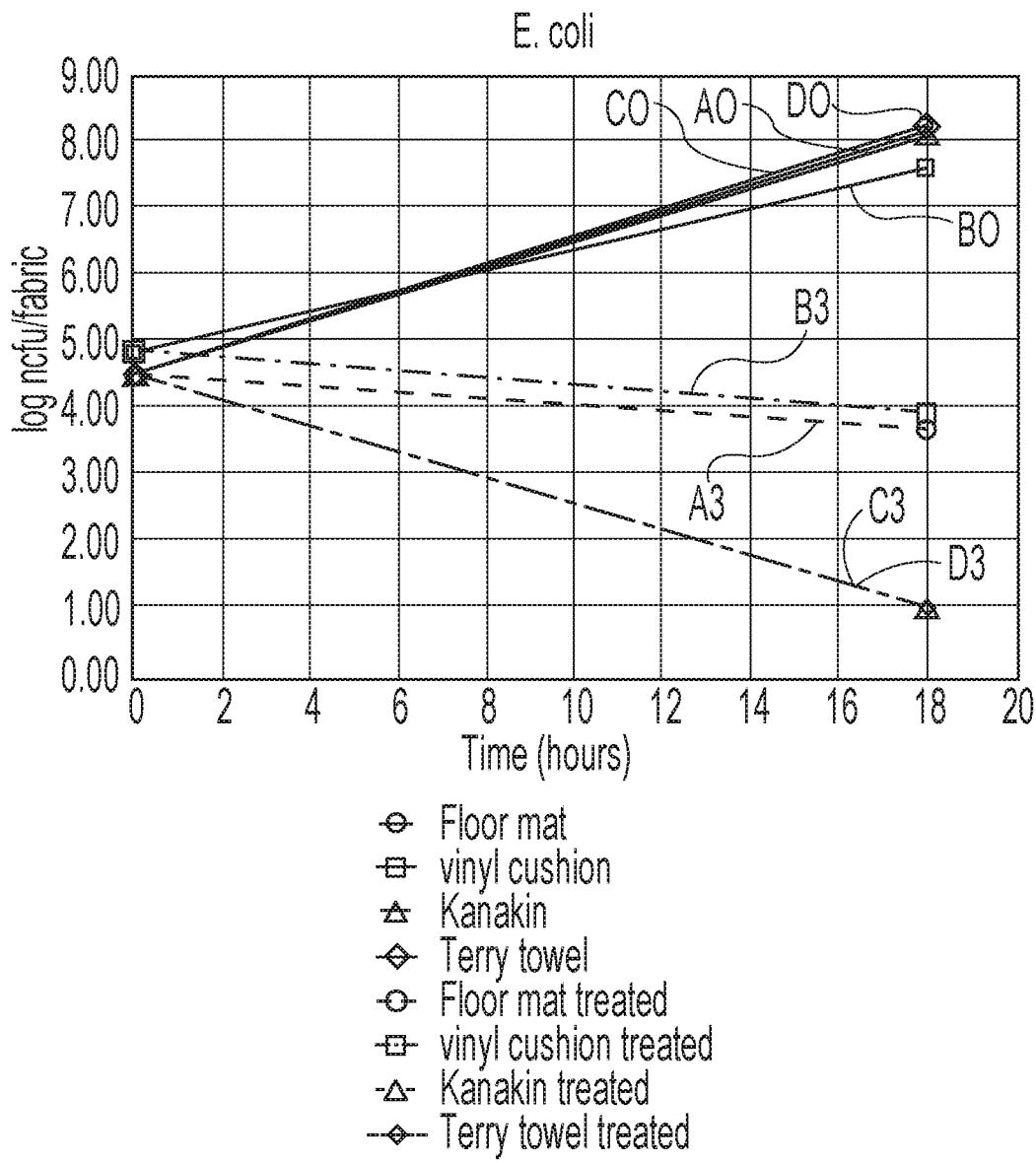
FIG. 15 is a graph plotting numbers of bacterial of different untreated test permeable materials and different test permeable materials treated with Inventive Air Freshening Product 3 against gram-negative bacterium (*E. coli*) as a function of time.

Table 11 below shows antibacterial activity value of Inventive Air Freshener Product 3 with Inventive Composition 3 having a mixture of 3% of C5 to C8 unbranched unsubstituted linear alkenal and 3% of C9 to C14 unbranched unsubstituted linear alkenal by weight of the composition. Inventive Composition 3 is applied to different Test Permeable Materials as shown below and assessed for antibacterial efficacy against Bacterium Sample 5 (*E. coli*). FIG. 15 is a corresponding graph of Table 11.

TABLE 11

Antibacterial Activity Value of Different Permeable Materials treated
with Inventive Composition 3 against Bacterium Sample 5 (*E. coli*)

| Samples | Number of bacteria at 0 hours ("Start Time") | Number of bacteria at 18 hours after Start Time | Antibacterial (AB)Activity Value |
|---|---|---|---|
| Untreated Permeable Material A0 | 4.40 | 8.15 | Ref |
| Untreated Permeable Material B0 | 4.72 | 7.61 | Ref |
| Untreated Permeable Material C0 | 4.40 | 8.07 | Ref |
| Untreated Permeable Material D0 | 4.40 | 8.20 | Ref |
| Treated Permeable Material A3 | 4.40 | 3.70 | 4.45 |
| Treated Permeable Material B3 | 4.72 | 3.86 | 3.75 |
| Treated Permeable Material C3 | 4.40 | 1.00 | 7.07 |
| Treated Permeable Material D3 | 4.40 | 1.00 | 7.20 |

Referring to Table 11 above, the above results show that an inventive freshening composition comprising trans-2-hexenal and trans-2-decenal in a respective level of 3% by weight of the composition demonstrate an antibacterial activity value of at least 3 on each of the different test permeable materials for Bacterium Sample 5 (*E. coli*).

Referring to FIG. 15, each of the Treated Permeable Materials show decreased bacteria number of *E. coli* and high antibacterial activity values relative to the corresponding Untreated Permeable Materials.

In particular, the results for a Treated Permeable Material D (terry towel material) show the highest antibacterial activity value for all the Inventive Air Freshening Products 1, 2, 3, 4 with the respective Inventive Compositions 1, 2, 3, 4. In an exemplary example, an advantage is that hand towels used for drying hands after washing are typically placed in the toilet for a period of time and there is repeated use of the hand towel. Providing an air freshening product according to the present invention in the toilet prevents bacterial growth on the hand towels.

Overall, the above results of decreased number of each bacterium on permeable materials treated with inventive compositions according to the present invention and a high antibacterial activity value for each of the treated permeable materials show that providing an inventive air freshening product according to the present invention in an interior environment such as for example a toilet environment achieves a technical effect of preventing bacteria growth on a surface comprising a permeable material having a bacterium deposited thereon. Consequently, by preventing bacteria growth, bacterial malodor may be reduced accordingly thereby enabling dual benefits of freshening and bacteria growth prevention in the interior environment.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An antibacterial air freshening product for an interior environment, wherein the interior environment is a finite volume of space in a non-vehicle environment, the product comprising:
   a container containing 1 ml to 50 ml of a freshening composition in fluid communication with a delivery member configured to contain a liquid phase of the composition-and allow the liquid phase of the composition to evaporate therefrom;
   wherein the composition is free of a surfactant and comprises:
      from 0.5% to 20% of a volatile aldehyde mixture, by weight of the composition;
   wherein the volatile aldehyde mixture consists of:
      a C5 to C8 unbranched unsubstituted linear alkenal selected from the group consisting of: 2-penten-1-al, 3-penten-1-al, 4-penten-1-al, (E)-2-hexen-1-al, (Z)-2-hexen-1-al, 3-hexen-1-al, 4-hexen-1-al, 2-hepten-1-al, 3-hepten-1-al, 4-hepten-1-al, 2-octen-1-al, 3-octen-1-al, 4-octen-1-al, and mixtures thereof; and
      a C9 to C14 unbranched unsubstituted linear alkenal selected from the group consisting of: 2-nonen-1-al, 3-nonen-1-al, 4-nonen-1-al, 5-nonen-1-al, 2-decen-1-al, 3-decen-1-al, 4-decen-1-al, 5-decen-1-al, 2-undecen-1-al, 3-undecen-1-al, 4-undecen-1-al, 5-undecen-1-al, 2-dodecen-1-al, 3-dodecen-1-al, 4-dodecen-1-al, 5-dodecen-al-1, 2-tridecen-1-al, 3-tridecen-1-al, 4-tridecen-1-al, 2-tetradecen-1-al, 3-tetradecen-1-al, 4-tetradecen-1-al, 5-tetradecen-1-al and mixtures thereof,
   wherein a weight ratio of the C5 to C8 unbranched unsubstituted linear alkenal to the C9 to C14 unbranched unsubstituted linear alkenal is from 3:1 to 1:3.

2. The product according to claim 1, wherein the C9-C14 unbranched unsubstituted linear alkenal has a (E)-2 C9-C14 unbranched unsubstituted linear alkenal.

3. The product according to claim 1, wherein the C5-C8 unbranched unsubstituted linear alkenal has a (E)-2 C5-C8 unbranched unsubstituted linear alkenal.

4. The product according to claim 1, wherein the C9-C14 unbranched unsubstituted linear alkenal comprises only one double bond.

5. The product according to claim 1, wherein the C5-C8 unbranched unsubstituted linear alkenal comprises only one double bond.

6. The product according to claim 1, wherein the composition comprises from 3%-5% C9-C14 unbranched unsubstituted linear alkenal by weight of the composition.

7. The product according to claim 1, wherein the composition comprises from 3%-5% C5-C8 unbranched unsubstituted linear alkenal by weight of the composition.

8. The product according to claim 1, wherein the C9-C14 unbranched unsubstituted linear alkenal is a C10 unbranched unsubstituted linear alkenal.

9. The product according to claim 1, wherein the C5-C8 unbranched unsubstituted linear alkenal is a C6 unbranched unsubstituted linear alkenal.

10. The product according to claim 1, wherein 2-decen-1-al is obtained from the group selected from: coriander leaf essential oil and blends thereof.

11. The product according to claim 1, wherein (E)-2-hexen-1-al is obtained from the group selected from: olive leaf essential oil, and blends thereof.

12. The product according to claim 1, wherein the weight ratio of the C5-C8 unbranched unsubstituted linear alkenal to the C9-C14 unbranched unsubstituted linear alkenal is 1:1.

13. The product according to claim 1, wherein the interior environment is the bathroom or the toilet.

14. The product according to claim 1, wherein the interior environment comprises a surface having a permeable material selected from the group consisting of: terry towel, cotton, vinyl and combinations thereof.

15. The product according to claim 1, wherein the delivery member is a membrane, wherein the membrane comprises an evaporative surface area from 6 $cm^2$ to 27 $cm^2$.

16. The product according to claim 1, further comprising:
a device having a housing comprising a rear frame having a frame opening and one or more apertures spaced from the frame opening;
an actuator movable relative to the rear frame; wherein:
the container is disposed within the housing, the container including a reservoir containing the composition, a rupturable substrate attached to and covering the reservoir and a rupture element aligned with the actuator to:
upon activation of the actuator, the rupture element ruptures the rupturable substrate, whereby at least a part of the volatile aldehyde mixture vaporises and exits the one or more apertures of the rear frame to enter the environment.

17. The product according to claim 16, wherein:
the actuator is a push button movably disposed within the frame opening of the rear frame,
the delivery member is a membrane, and
the membrane is disposed adjacent the rupturable substrate and aligned with the push button.

* * * * *